United States Patent
Shelton, IV et al.

(10) Patent No.: US 10,163,309 B1
(45) Date of Patent: Dec. 25, 2018

(54) SURGICAL INSTRUMENT WITH INTEGRATED AND INDEPENDENTLY POWERED DISPLAYS

(71) Applicant: ETHICON LLC, Guaynabo, PR (US)

(72) Inventors: Frederick E. Shelton, IV, Hillsboro, OH (US); Michael J. Vendely, Lebanon, OH (US); Jason L. Harris, Lebanon, OH (US); Brett E. Swensgard, West Chester, OH (US); Michael D. Auld, Blue Ash, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/634,418

(22) Filed: Jun. 27, 2017

(51) Int. Cl.
  *G08B 5/22* (2006.01)
  *A61B 34/00* (2016.01)
  (Continued)

(52) U.S. Cl.
  CPC .............. *G08B 5/22* (2013.01); *A61B 34/25* (2016.02); *A61B 17/072* (2013.01); *A61B 17/07207* (2013.01); *A61B 17/1155* (2013.01); *A61B 2017/0046* (2013.01); *A61B 2017/00464* (2013.01); *A61B 2017/00734* (2013.01)

(58) Field of Classification Search
  CPC ... G08B 5/22; G06F 19/3406; G06F 19/3412; H01M 2010/4278; H01M 2010/4271; H01M 10/425; H01M 2220/30; A61B 17/042; A61B 17/07207; A61B 17/1155; A61B 17/00; A61B 17/064; A61B 17/068; A61B 90/00; A61B 90/06; A61B 90/08; A61B 2090/0803; A61B 2090/0807; A61B 2017/0046; A61B 2017/00464; A61B 2017/00734; A61B 2017/00398; A61B 2017/00017; A61B 2017/00367; A61B 2017/00115; A61B 2017/00119;
  (Continued)

(56) References Cited

U.S. PATENT DOCUMENTS

| | | | |
|---|---|---|---|
| 6,432,046 B1 * | 8/2002 | Yarush | A61B 1/00039 600/109 |
| 6,554,765 B1 * | 4/2003 | Yarush | A61B 1/00039 348/73 |

(Continued)

OTHER PUBLICATIONS

U.S. Appl. No. 15/634,385, filed Jun. 27, 2017.
(Continued)

*Primary Examiner* — Mohamed Barakat
(74) *Attorney, Agent, or Firm* — Frost Brown Todd LLC

(57) ABSTRACT

A surgical instrument includes a handle assembly, a graphical user interface, a primary circuit, a first power source, a life display, and a secondary circuit. The graphical user interface is disposed on the handle assembly. The primary circuit is operable to drive the graphical user interface. The first power source is configured to provide power to the graphical user interface. The life display is disposed on the handle assembly and is operable to display a power level of the primary power source. The secondary circuit is operable to drive the life display. The secondary circuit is separate from the primary circuit. The secondary circuit is configured to draw less power to drive the life display than an amount of power required by the first power source to drive the graphical user interface.

20 Claims, 22 Drawing Sheets

(51) Int. Cl.
*A61B 17/00* (2006.01)
*A61B 17/072* (2006.01)
*A61B 17/115* (2006.01)

(58) Field of Classification Search
CPC ........... A61B 2017/00225; A61B 2017/00681; A61B 2017/00725; A61B 2017/00199
See application file for complete search history.

(56) References Cited

U.S. PATENT DOCUMENTS

| | | | |
|---|---|---|---|
| 6,783,524 B2 | 8/2004 | Anderson et al. | |
| 7,000,818 B2 | 2/2006 | Shelton, IV et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,408,439 B2 | 4/2013 | Huang et al. | |
| 8,415,045 B2* | 4/2013 | Miyajima | H01M 2/021 429/91 |
| 8,453,643 B2* | 6/2013 | Sanchez | A61M 16/024 128/200.24 |
| 8,453,914 B2 | 6/2013 | Laurent et al. | |
| 8,460,182 B2* | 6/2013 | Ouyang | A61B 10/0275 348/77 |
| 9,072,535 B2 | 7/2015 | Shelton, IV et al. | |
| 9,186,142 B2 | 11/2015 | Fanelli et al. | |
| 9,520,720 B2* | 12/2016 | Perry | H01M 10/4207 |
| 9,717,497 B2 | 8/2017 | Zerkle et al. | |
| 9,795,379 B2 | 10/2017 | Leimbach et al. | |
| 9,808,248 B2 | 10/2017 | Hoffman | |
| 2006/0135198 A1* | 6/2006 | Lee | H04M 1/72522 455/550.1 |
| 2010/0130260 A1* | 5/2010 | Naruse | H04M 1/0256 455/566 |
| 2011/0068941 A1* | 3/2011 | Nunomaki | H01M 10/48 340/636.1 |
| 2012/0192001 A1* | 7/2012 | Sutardja | G06F 1/1616 713/323 |
| 2014/0165796 A1* | 6/2014 | Gauthier | A61B 17/8875 81/479 |
| 2014/0263541 A1 | 9/2014 | Leimbach et al. | |
| 2015/0272575 A1* | 10/2015 | Leimbach | A61B 17/072 227/175.3 |
| 2015/0280384 A1 | 10/2015 | Leimbach et al. | |
| 2015/0297200 A1* | 10/2015 | Fitzsimmons | A61B 17/00 606/1 |
| 2016/0018790 A1* | 1/2016 | Su | G04G 17/02 368/316 |
| 2016/0066912 A1* | 3/2016 | Baber | A61B 17/32 307/64 |
| 2016/0066913 A1* | 3/2016 | Swayze | A61B 17/072 227/176.1 |
| 2016/0249916 A1* | 9/2016 | Shelton, IV | G06F 19/327 705/2 |
| 2016/0256184 A1* | 9/2016 | Shelton, IV | A61B 17/068 |
| 2016/0310134 A1* | 10/2016 | Contini | A61B 17/07207 |
| 2017/0086823 A1 | 3/2017 | Leimbach et al. | |
| 2017/0207467 A1* | 7/2017 | Shelton, IV | A61B 17/320092 |
| 2017/0312044 A1 | 11/2017 | Conlon et al. | |
| 2017/0367726 A9* | 12/2017 | Smith | A61B 17/320068 |

OTHER PUBLICATIONS

U.S. Appl. No. 15/634,436, filed Jun. 27, 2017.
U.S. Appl. No. 15/634,452, filed Jun. 27, 2017.
U.S. Appl. No. 15/634,475, filed Jun. 27, 2017.
U.S. Appl. No. 15/634,497, filed Jun. 27, 2017.
U.S. Appl. No. 15/634,524, filed Jun. 27, 2017.
U.S. Appl. No. 15/634,556, filed Jun. 27, 2017.
U.S. Appl. No. 15/634,589, filed Jun. 27, 2017.
U.S. Appl. No. 15/634,620, filed Jun. 27, 2017.

* cited by examiner

SURGICAL INSTRUMENT WITH INTEGRATED AND INDEPENDENTLY POWERED DISPLAYS

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in various ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,000,818, entitled "Surgical Stapling Instrument Having Separate Distinct Closing and Firing Systems," issued Feb. 21, 2006; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, now U.S. Pat. No. 9,186,142, issued Nov. 17, 2015; U.S. Patent Application Publication No. 2014/0239041, entitled "Lockout Feature for Movable Cutting Member of Surgical Instrument," Published Aug. 28, 2014, now U.S. Pat. No. 9,717,497, issued Aug. 1, 2017; U.S. Patent Application Publication No. 2014/0239038, entitled "Surgical Instrument with Multi-Diameter Shaft," published Aug. 28, 2014, now U.S. Pat. No. 9,795,379, issued Oct. 24, 2017; and U.S. Patent Application Publication No. 2014/0239044, entitled "Installation Features for Surgical Instrument End Effector Cartridge," published Aug. 28, 2014, now U.S. Pat. No. 9,808,248, issued Nov. 7, 2017. The disclosure of each of the above-cited U.S. Patent Applications is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
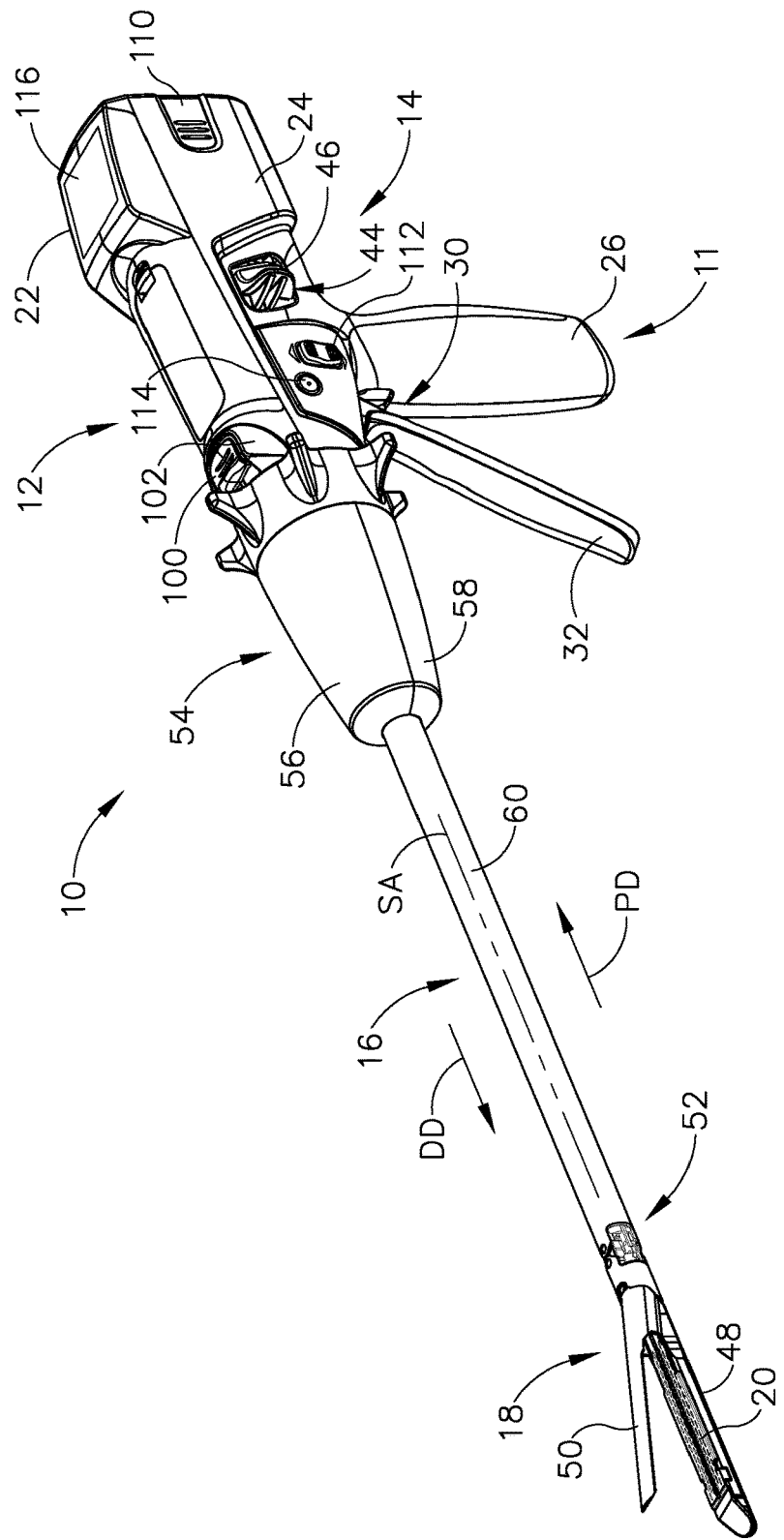
FIG. 1 depicts a perspective view of an exemplary surgical instrument including an interchangeable shaft assembly and a handle assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Although the surgical instruments described herein comprise motorized implements for cutting and stapling, it will be appreciated that the configurations described herein may be used with any suitable type of electrical surgical instrument such as cutters, claspers, staplers, RF cutter/coagulators, ultrasonic cutter/coagulators, and laser cutter/coagulators, for example.

I. Overview of Exemplary Surgical Instrument

FIG. 1 depicts a motor-driven surgical cutting and fastening instrument (10) that includes a handle assembly (11) and a removable shaft assembly (16). In some versions, handle assembly (11) and shaft assembly (16) are each provided a single-use, disposable components. In some other versions, handle assembly (11) and shaft assembly (16) are each provided as reusable components. As another merely illustrative example, shaft assembly (16) may be provided as a single-use, disposable component while handle assembly is provided as a reusable component. Various suitable ways in which reusable versions of handle assembly (11) and shaft assembly (16) may be suitable reprocessed for reuse will be apparent to those of ordinary skill in the art in view of the teachings herein.

Handle assembly (11) of the present example includes a housing (12), a closure trigger (32), and a firing trigger (33). At least a portion of housing (12) forms a handle (14) that is configured to be grasped, manipulated and actuated by the clinician. Housing (12) is configured for operative attachment to shaft assembly (16), which has a surgical end effector (18) operatively coupled thereto. As described below, end effector (18) is configured to perform one or more surgical tasks or procedures. In particular, end effector (18) of the example shown in FIG. 1 is operable to perform a surgical cutting and stapling procedure, in a manner similar to an end effector of a conventional endocutter, though it should be understood that this is just one merely illustrative example.

Figure 2:
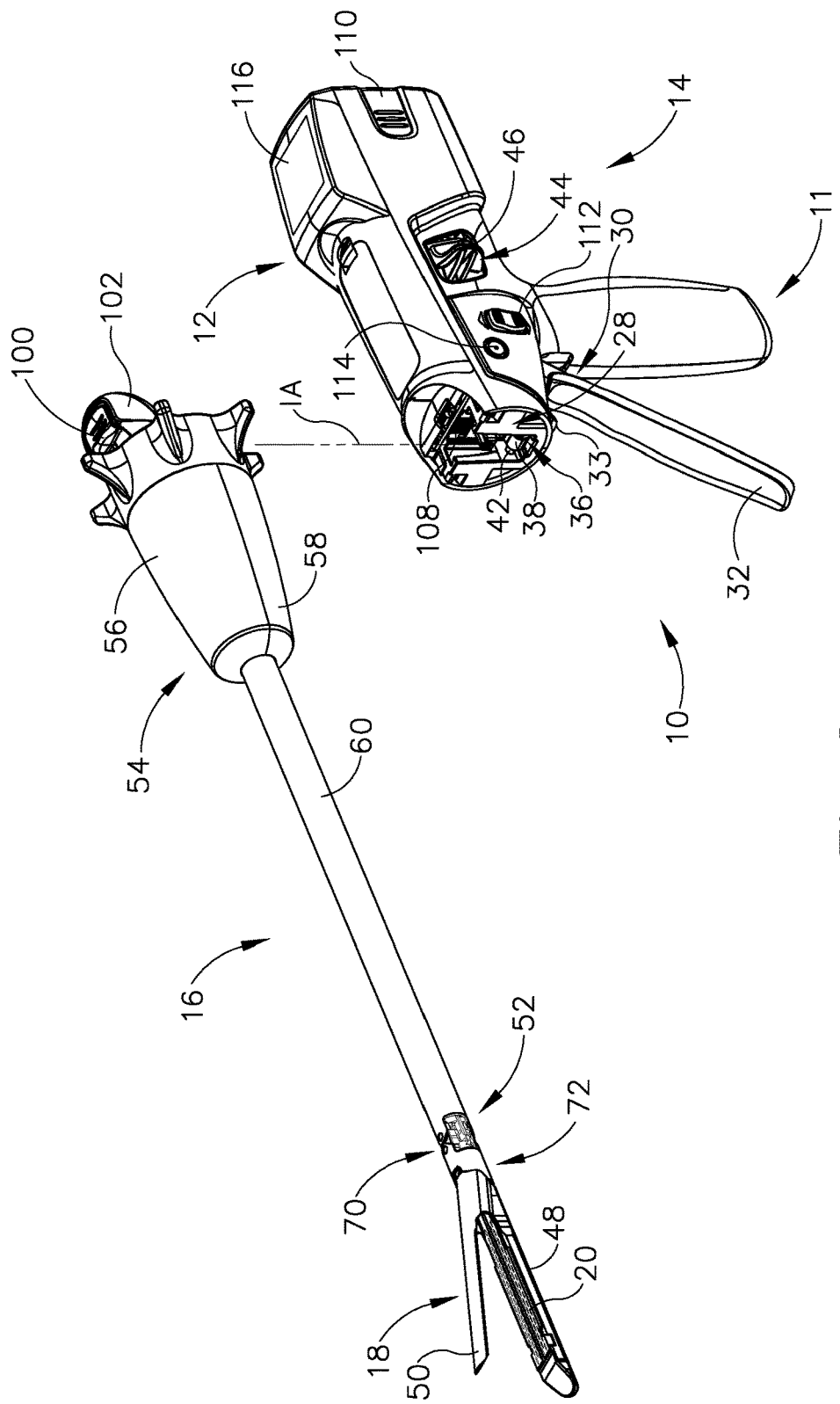
FIG. 2 depicts a perspective view of the instrument of FIG. 1, showing the shaft assembly disassembled from the handle assembly of the instrument.
Figure 3:
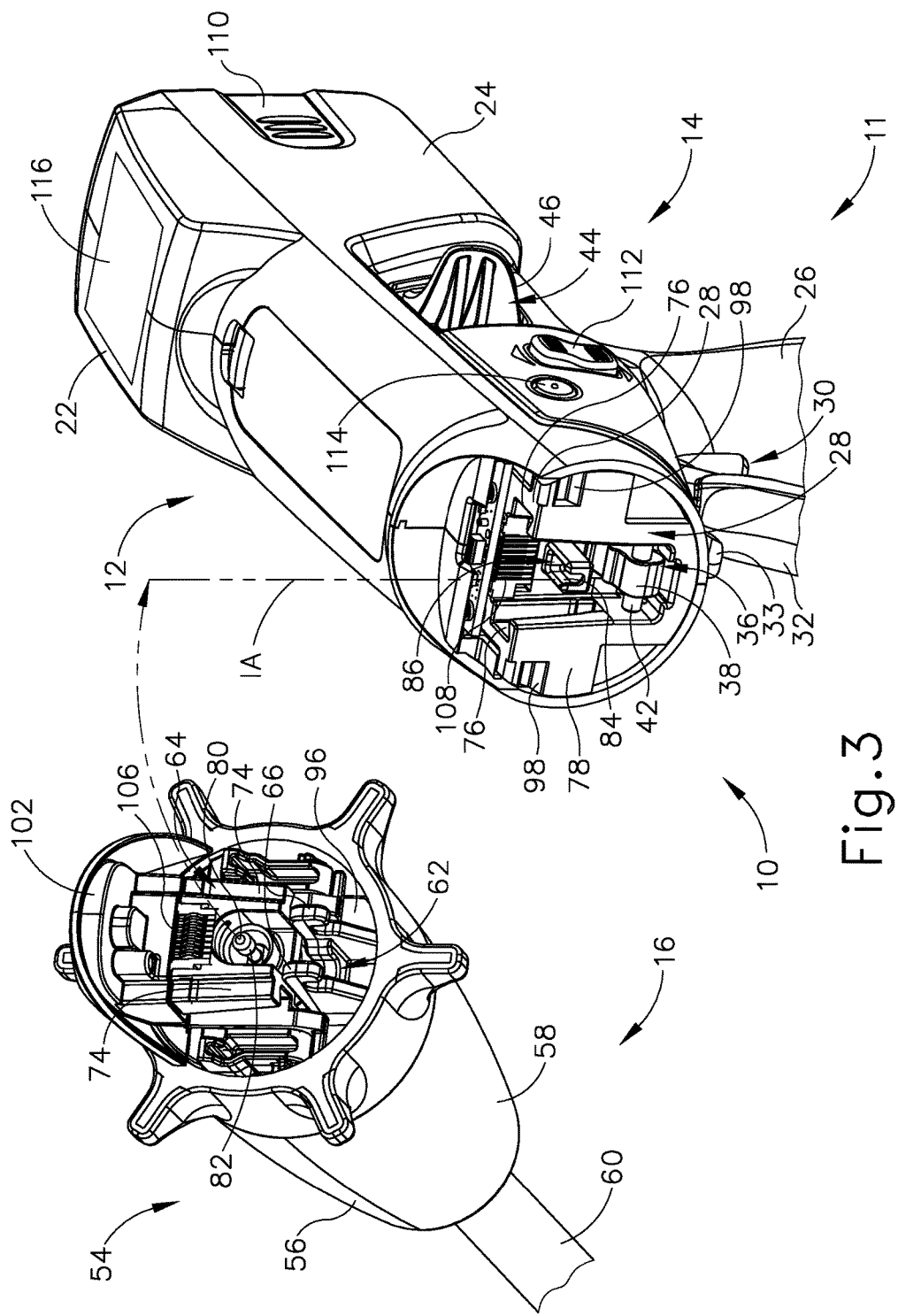
FIG. 3 depicts a partial perspective view of the instrument of FIG. 1, showing the shaft assembly disassembled from the handle assembly of the instrument.

FIG. 1 illustrates surgical instrument (10) with interchangeable shaft assembly (16) operatively coupled to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be grasped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto. As will also be discussed in further detail below, triggers (32, 33) are pivotable toward pistol grip portion (26) to activate at least some of the drive systems in handle (14).

Figure 5:
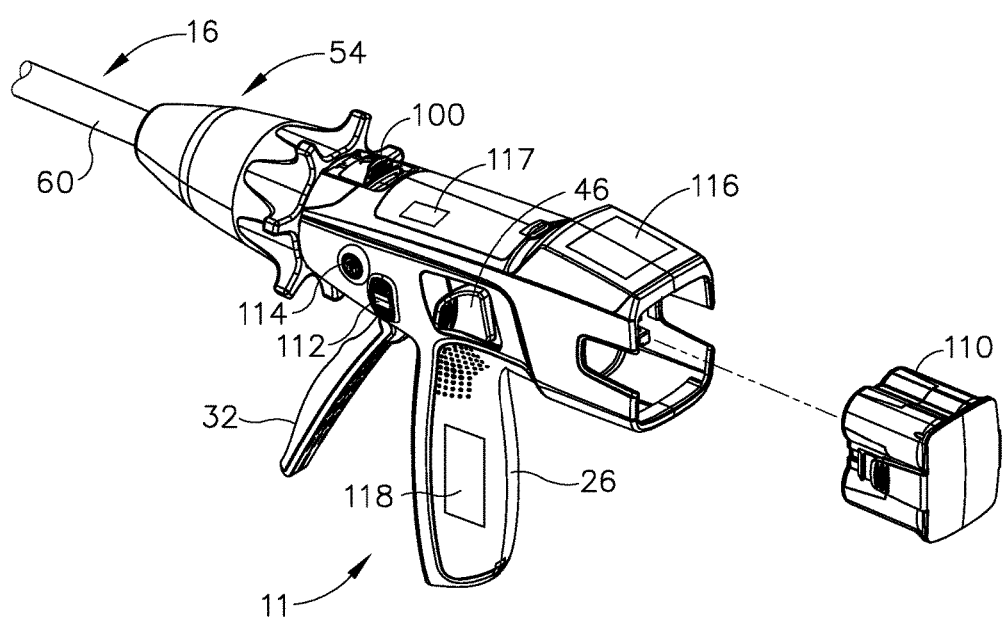
FIG. 5 depicts a perspective view of a proximal portion of the instrument of FIG. 1, with a battery removed from the handle assembly.

At least some of the drive systems in handle assembly (11) are ultimately driven by a motor (118), which is shown schematically in FIG. 5. In the present example, motor (118) is located in pistol grip portion (26), though it should be understood that motor (118) may be located at any other suitable position. Motor (118) receives power from a battery pack (110), which is secured to handle (14). In the present example, and as shown in FIG. 5, battery pack (110) is removable from handle (14). In some other versions, battery pack (110) is not removable from handle (14). In some such versions, battery pack (110) (or a variation thereof) is fully contained within handle housing segments (22, 24). Various suitable forms that motor (118) and battery pack (110) may take will be apparent to those of ordinary skill in the art in view of the teachings herein.

As also shown schematically in FIG. 5, a control circuit (117) is contained within handle (14). By way of example only, control circuit (117) may comprise a microcontroller and/or various other components as will be apparent to those of ordinary skill in the art in view of the teachings herein. Control circuit (117) is configured to store and execute control algorithms to drive motor (118). Control circuit (117) is also configured to drive a graphical user interface (116), which is located at the proximal end of handle assembly (11). In some versions, control circuit (117) is configured to receive and process one or more signals from shaft assembly (16). By way of example only, control circuit (117) may be configured and operable in accordance with at least some of the teachings of U.S. Pub. No. 2015/0272575, entitled "Surgical Instrument Comprising a Sensor System," published Oct. 1, 2015, now U.S. Pat. No. 9,913,642, issued Mar. 13, 2018, the disclosure of which is incorporated by reference herein. Other suitable ways in which control circuit (117) may be configured and operable will be apparent to those of ordinary skill in the art in view of the teachings herein.

As best seen in FIG. 3, a frame (28) of handle (14) operatively supports a plurality of drive systems. In this particular example, frame (28) operatively supports a "first" or closure drive system, generally designated as (30), which may be employed to apply closing and opening motions to interchangeable shaft assembly (16) that is operatively attached or coupled thereto. Also in this particular example, closure drive system (30) includes an actuator in the form of a closure trigger (32) that is pivotally supported by frame (28). More specifically, closure trigger (32) is pivotally coupled to housing (14) by a pin (not shown). Such arrangement enables closure trigger (32) to be manipulated by a clinician such that when the clinician grasps pistol grip portion (26) of handle (14), closure trigger (32) may be easily pivoted from a starting or "unactuated" position (FIG. 4A) toward pistol grip portion (26) to an "actuated" position; and more particularly to a fully compressed or fully actuated position (FIG. 4B). Closure trigger (32) may be biased into the unactuated position by spring or other biasing arrangement (not shown).

In the present example, closure drive system (30) further includes a closure linkage assembly (36) pivotally coupled to closure trigger (32). A portion of closure linkage assembly (36) is shown in FIG. 3. Closure linkage assembly (36) may include a first closure link (not shown) and a second closure link (38) that are pivotally coupled to closure trigger (32) by a pin (not shown). Second closure link (38) may also be referred to herein as an "attachment member" and includes a transverse attachment pin (42). As shown in FIG. 3, attachment pin (42) is exposed when shaft assembly (16) is detached from handle assembly (11). Attachment pin (42) may thus couple with a complementary feature of a shaft assembly (16) when shaft assembly (16) is coupled with handle assembly (11), as described in greater detail below.

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upwardly to a point where a locking pawl (not shown) drops into retaining engagement with first closure link (not shown), thereby preventing closure trigger (32) from returning to the unactuated position. Thus, closure release assembly (44) serves to lock closure trigger (32) in the fully actuated position.

When the clinician desires to unlock closure trigger (32) from the actuated position to return to the unactuated position, the clinician simply pivots closure release button assembly (46) by urging release button assembly (46) distally, such that locking pawl (not shown) is moved out of engagement with the first closure link (not shown). When the locking pawl (not shown) has been moved out of engagement with first closure link (not shown), closure trigger (32) may return back to the unactuated position in response to a resilient bias urging closure trigger (32) back to the unactuated position. Other closure trigger locking and release arrangements may also be employed.

Interchangeable shaft assembly (16) further includes an articulation joint (52) and an articulation lock (not shown) that can be configured to releasably hold end effector (18) in a desired position relative to a longitudinal axis of shaft assembly (16). In the present example, articulation joint (52) is configured to allow end effector (18) to be laterally deflected away from the longitudinal axis of shaft assembly (16), as is known in the art. By way of example only, end effector (18), articulation joint (52), and the articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014, now abandoned.

In the present example, articulation at articulation joint (52) is motorized via motor (118), based on control input from the operator via an articulation control rocker (112) on handle assembly (11). By way of example only, when the operator presses on the upper portion of articulation control rocker (112), end effector (18) may laterally pivot to the right (viewing instrument (10) from above) at articulation joint (52); and when the operator presses on the lower portion of articulation control rocker (112), end effector (18) may laterally pivot to the left (viewing instrument (10) from above) at articulation joint (52). In some versions, the other side of handle assembly (11) includes another articulation control rocker (112). In such versions, the articulation control rocker (112) on the other side of handle assembly (11) may be configured to provide pivoting of end effector (18) in directions opposite to those listed above in response to upper actuation of articulation control rocker (112) and lower actuation of articulation control rocker (112). By way of example only, articulation control rocker (112) and the rest of the features that provide motorized articulation of end effector (18) at articulation joint (52) may be configured and operable in accordance with at least some of the teachings of U.S. Pub. No. 2015/0280384, entitled "Surgical Instrument Comprising a Rotatable Shaft," published Oct. 1, 2015, the disclosure of which is incorporated by reference herein. Other suitable ways in which articulation control rocker (112) and the rest of the features that provide motorized articulation of end effector (18) at articulation joint (52) may be configured and operable will be apparent to those of ordinary skill in the art in view of the teachings herein.

End effector (18) of the present example comprises a lower jaw in the form of an elongated channel (48) that is configured to operatively a support staple cartridge (20) therein. End effector (18) of the present example further includes an upper jaw in the form of an anvil (50) that is pivotally supported relative to elongated channel (48). Interchangeable shaft assembly (16) further includes a proximal housing or nozzle (54) comprised of nozzle portions (56, 58); and a closure tube (60) that can be utilized to close and/or open anvil (50) of end effector (18). Shaft assembly (16) also includes a closure shuttle (62) that is slidably supported within a chassis (64) of shaft assembly (16) such that closure shuttle (62) may be axially moved relative to chassis (64). Closure shuttle (62) includes a pair of proximally-protruding hooks (66) that are configured for attachment to attachment pin (42) that is attached to second closure link (38). A proximal end (not shown) of closure tube (60) is coupled to closure shuttle (62) for relative rotation thereto, though the coupling of closure tube (60) with closure shuttle (62) provides that closure tube (60) and closure shuttle (62) will translate longitudinally with each other. A closure spring (not shown) is journaled on closure tube (60) and serves to bias closure tube (60) in the proximal direction (PD), which can serve to pivot closure trigger (32) into the unactuated position when shaft assembly (16) is operatively coupled to handle (14).

In the present example, articulation joint (52) includes a double pivot closure sleeve assembly (70). Double pivot closure sleeve assembly (70) includes an end effector closure sleeve assembly (72) for engaging an opening tab on anvil (50) in the various manners described in U.S. Pub. No. 2014/0263541, now abandoned, the disclosure of which is incorporated by reference herein. It should be understood that double pivot closure sleeve assembly (70) is coupled with closure tube (60) such that double pivot closure sleeve assembly (70) translates with closure tube (60) in response to pivotal movement of closure trigger (32), even when articulation joint (52) is in an articulated state (i.e., when end effector (18) is pivotally deflected laterally away from the longitudinal axis of shaft assembly (16) at articulation joint (52)). Moreover, the engagement of end effector closure sleeve assembly (72) with anvil (50) provides pivotal movement of anvil (50) toward staple cartridge (20) in response to distal translation of double pivot closure sleeve assembly (70) and closure tube (60); and pivotal movement of anvil (50) away from staple cartridge (20) in response to proximal translation of double pivot closure sleeve assembly (70) and closure tube (60). While shaft assembly (16) of the present example includes articulation joint (52), other interchangeable shaft assemblies may lack articulation capabilities.

As shown in FIG. 3, chassis (64) includes a pair of tapered attachment portions (74) formed thereon that are adapted to be received within corresponding dovetail slots (76) formed within a distal attachment flange portion (78) of frame (28). Each dovetail slot (76) may be tapered or generally V-shaped to seatingly receive attachment portions (74) therein. A shaft attachment lug (80) is formed on the proximal end of an intermediate firing shaft (82). Thus, when interchangeable shaft assembly (16) is coupled to handle (14), shaft attachment lug (80) is received in a firing shaft attachment cradle (84) formed in a distal end of a longitudinal drive member (86). When shaft attachment lug (80) is received in firing shaft attachment cradle (84), intermediate firing shaft (82) will translate longitudinally with longitudinal drive member (86). When intermediate firing shaft (82) translates distally, intermediate firing shaft (82) actuates end effector (18) to drive staples into tissue and cut the tissue, as is known in the art. By way of example only, this actuation of end effector (18) may be carried out in accordance with at least some of the teachings of U.S. Pub. No. 2015/0280384, the disclosure of which is incorporated by reference herein; and/or in accordance with the teachings of various other references cited herein.

Figure 4A:
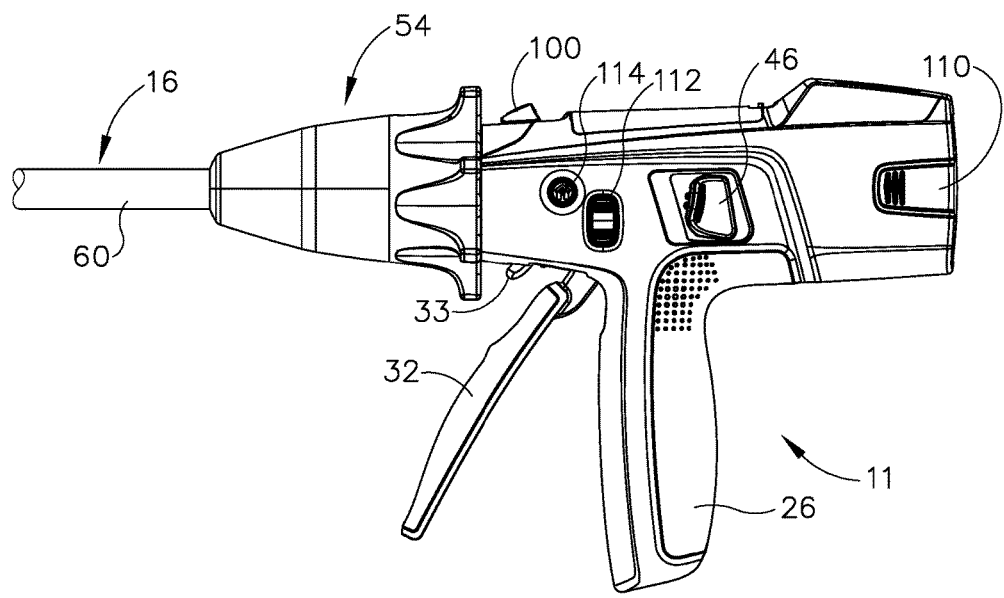
FIG. 4A depicts a side elevational view of a proximal portion of the instrument of FIG. 1, with a closure trigger in a first pivotal position and a firing trigger in a first pivotal position.
Figure 4B:
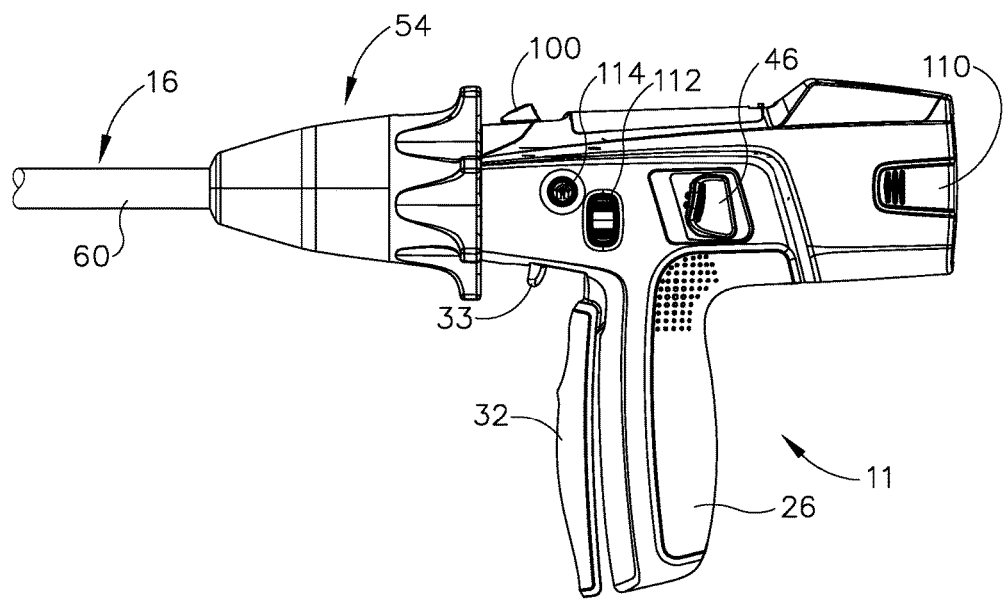
FIG. 4B depicts a side elevational view of a proximal portion of the instrument of FIG. 1, with the closure trigger in a second pivotal position and the firing trigger in a second pivotal position.
Figure 4C:
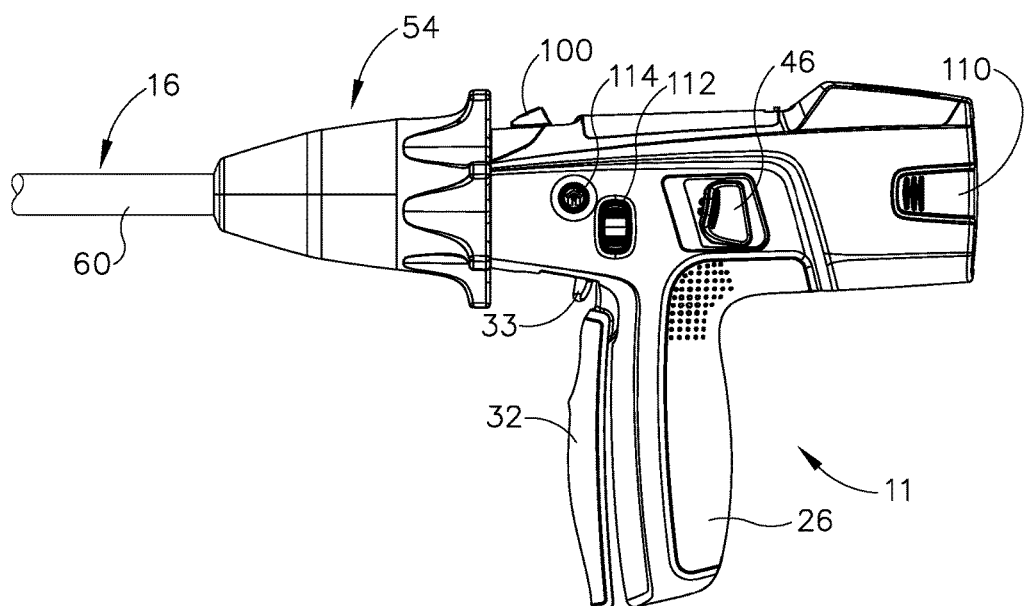
FIG. 4C depicts a side elevational view of a proximal portion of the instrument of FIG. 1, with the closure trigger in the second pivotal position and the firing trigger in a third pivotal position.

FIGS. 4A-4C show the different states of handle assembly (11) during the different states of actuation of end effector (18). In FIG. 4A, handle assembly (11) is in a state where closure trigger (32) is in a non-actuated pivotal position and firing trigger (33) is in a non-actuated pivotal position. At this stage, end effector (18) is in an opened state where anvil (50) is pivoted away from staple cartridge (20).

In FIG. 4B, handle assembly (11) is in a state where closure trigger (32) is in an actuated pivotal position. As noted above, closure trigger (32) will be locked in this position until the operator actuates release button assembly (46). At this stage, end effector is in a closed but unfired state where anvil (50) is pivoted toward staple cartridge (20), such that tissue is being compressed between anvil (50) and cartridge (20). However, firing shaft (82) has not yet been driven distally to actuate staples from staple cartridge (20), and the knife at the distal end of firing shaft (82) has not yet severed the tissue between anvil (20) and staple cartridge (20). It should be noted that firing trigger (33) is in a partially-actuated pivotal position in FIG. 4B, due to the travel of closure trigger (32) from the non-actuated pivotal position to the actuated pivotal position. However, this movement of firing trigger (33) is only provided in order to improve access to firing trigger (33) for the operator. In other words, this movement of firing trigger (33) from the position shown in FIG. 4A to the position shown in FIG. 4B does not yet activate a firing sequence.

In FIG. 4C, handle assembly is in a state where closure trigger (32) remains in the actuated pivotal position, and firing trigger (33) has been pivoted to an actuated pivotal position. This actuation of firing trigger (33) activates motor (118) to drive longitudinal drive member (86) longitudinally, which in turn drives firing shaft (82) longitudinally. The longitudinal movement of firing shaft (82) results in actuation of staples from staple cartridge (20) into the tissue compressed between anvil (50) and staple cartridge (20); and further results in the severing of the tissue compressed between anvil (50) and staple cartridge (20). In some versions, an additional safety trigger is provided. For instance, the additional safety trigger may prevent actuation of firing trigger (33) until the safety trigger is actuated. In other words, after reaching the state shown in FIG. 4B, when the operator is ready to actuate firing trigger (33), the operator must first actuate the safety trigger and then actuate firing trigger (33). It should be understood that the presence of a safety trigger may prevent inadvertent actuation of firing trigger (33).

It should also be understood that, in the present example, the actuation of anvil (50) toward staple cartridge (20) is provided through purely mechanical couplings between closure trigger (32) and anvil (50), such that motor (118) is not used to actuate anvil (50). It should also be understood that, in the present example, the actuation of firing shaft (82) (and, hence, the actuation of staple cartridge (20)) is provided through activation of motor (118). In addition, the actuation of articulation joint (52) is provided through activation of motor (118) in the present example. This motorized actuation of articulation joint (52) is provided via longitudinal translation of drive member (86). A clutch assembly (not shown) within shaft assembly (16) is operable to selectively couple longitudinal translation of drive member (86) with features to either drive articulation joint (52) or actuate staple cartridge (20). Such selective coupling via the clutch assembly is based on the pivotal position of closure trigger (32). In particular, when closure trigger (32) is in the non-actuated position shown in FIG. 4A, activation of motor (118) (in response to activation of articulation control rocker (112)) will drive articulation joint (52). When closure trigger (32) is in the actuated position shown in FIG. 4B, activation of motor (118) (in response to actuation of firing trigger (33)) will actuate staple cartridge (20). By way of example only, the clutch assembly may be configured and operable in accordance with at least some of the teachings of U.S. Pub. No. 2015/0280384, the disclosure of which is incorporated by reference herein.

In the present example, handle assembly (11) also includes a "home" button (114). By way of example only, when anvil (50) is in a closed position, "home" button (114) may be operable to activate motor (118) to retract drive member (86) proximally to a proximal-most, "home" position. In addition, or in the alternative, when anvil (50) is in an open position, "home" button (114) may be operable to activate motor (118) to drive articulation joint (52) to achieve a non-articulated state, such that end effector (18) is coaxially aligned with shaft assembly (16). In addition, or in the alternative, "home" button (114) may activate graphical user interface (116) to return to a "home" screen. Other suitable operations that may be provided in response to activation of "home" button (114) will be apparent to those of ordinary skill in the art in view of the teachings herein.

Shaft assembly (16) of the present example further includes a latch system for removably coupling shaft assembly (16) to handle assembly (11) and, more specifically, to frame (28). By way of example only, this latch system may include a lock yoke or other kind of lock member that is movably coupled to chassis (64). As shown in FIG. 3, such a lock yoke may include two proximally protruding lock lugs (96) that are configured for releasable engagement with corresponding lock detents or grooves (98) in frame (28). In some versions, the lock yoke is biased in the proximal direction by a resilient member (e.g., a spring, etc.). Actuation of the lock yoke may be accomplished by a latch button (100) that is slidably mounted on a latch actuator assembly (102) that is mounted to chassis (64). Latch button (100) may be biased in a proximal direction relative to the lock yoke. The lock yoke may be moved to an unlocked position by urging latch button (100) the in distal direction, which also causes the lock yoke to pivot out of retaining engagement with frame (28). When the lock yoke is in "retaining engagement" with frame (28), lock lugs (96) are retainingly seated within the corresponding lock detents or grooves (98). By way of further example only, shaft assembly (16) may be removably coupled with handle assembly (11) in accordance with at least some of the teachings of U.S. Pub. No. 2017/0086823, entitled "Surgical Stapling Instrument with Shaft Release, Powered Firing, and Powered Articulation," published Mar. 30, 2017, the disclosure of which is incorporated by reference herein; in accordance with at least some of the teachings of U.S. Pub. No. 2015/0280384, the disclosure of which is incorporated by reference herein; and/or in any other suitable fashion.

To commence the coupling process between shaft assembly (16) and handle assembly (11), the clinician may position chassis (64) of interchangeable shaft assembly (16) above or adjacent to frame (28) such that tapered attachment portions (74) formed on chassis (64) are aligned with dovetail slots (76) in frame (28). The clinician may then move shaft assembly (16) along an installation axis (IA) that is perpendicular to the longitudinal axis of shaft assembly (16) to seat attachment portions (74) in "operative engagement" with the corresponding dovetail receiving slots (76). In doing so, shaft attachment lug (80) on intermediate firing shaft (82) will also be seated in cradle (84) in the longitudinally movable drive member (86) and the portions of pin

(42) on second closure link (38) will be seated in the corresponding hooks (66) in closure shuttle (62). As used herein, the term "operative engagement" in the context of two components means that the two components are sufficiently engaged with each other so that upon application of an actuation motion thereto, the components may carry out their intended action, function, and/or procedure.

As discussed above, at least five systems of interchangeable shaft assembly (16) may be operatively coupled with at least five corresponding systems of handle (14). A first system comprises a frame system that couples and/or aligns the frame or spine of shaft assembly (16) with frame (28) of the handle (14). A second system is the latch system that releasably locks the shaft assembly (16) to the handle (14).

A third system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). Through closure drive system (30), anvil (50) pivots toward and away from staple cartridge (20) based on pivotal movement of closure trigger (32) toward and away from pistol grip (26).

A fourth system is an articulation and firing drive system operatively connecting firing trigger (33) of handle (14) with intermediate firing shaft (82) of the shaft assembly (16). As outlined above, the shaft attachment lug (80) operatively connects with the cradle (84) of the longitudinal drive member (86). This fourth system provides motorized actuation of either articulation joint (52) or staple cartridge (20), depending on the pivotal position of closure trigger (32). When closure trigger (32) is in a non-actuated pivotal position, the fourth system operatively connects articulation control rocker (112) with articulation joint (52), thereby providing motorized pivotal deflection of end effector (18) toward and away from the longitudinal axis of shaft assembly (16) at articulation joint (52). When closure trigger (32) is in an actuated pivotal position, the fourth system operatively connects firing trigger (33) with staple cartridge (20), resulting in stapling and cutting of tissue captured between anvil (50) and staple cartridge (20) in response to actuation of firing trigger (33).

A fifth system is an electrical system that can signal to control circuit (117) in handle (14) that the shaft assembly (16) has been operatively engaged with the handle (14), to conduct power and/or communicate signals between the shaft assembly (16) and the handle (14). In the present example, and as shown in FIG. 3, shaft assembly (16) includes an electrical connector (106) that is operatively mounted to a shaft circuit board (not shown). Electrical connector (106) is configured for mating engagement with a corresponding electrical connector (108) on a handle control board (not shown). Further details regarding the circuitry and control systems may be found in U.S. Pub. No. 2014/0263541, now abandoned, the disclosure of which is incorporated by reference herein and/or U.S. Pub. No. 2015/0272575, now U.S. Pat. No. 9,913,642, issued Mar. 13, 2018, the disclosure of which is incorporated by reference herein.

Other kinds of systems of interchangeable shaft assembly (16) that may be operatively coupled with at corresponding systems of the handle (14) will be apparent to those of ordinary skill in the art in view of the teachings herein.

As noted above, handle assembly (11) of the present example includes a graphical user interface (116). By way of example only, graphical user interface (116) may be used to display various information about the operational state of battery pack (110), the operational state of end effector (18), the operational state of articulation joint (52), the operational state of triggers (32, 33), and/or any other kinds of information. Other suitable kinds of information that may be displayed via graphical user interface will be apparent to those of ordinary skill in the art in view of the teachings herein.

Figure 6:
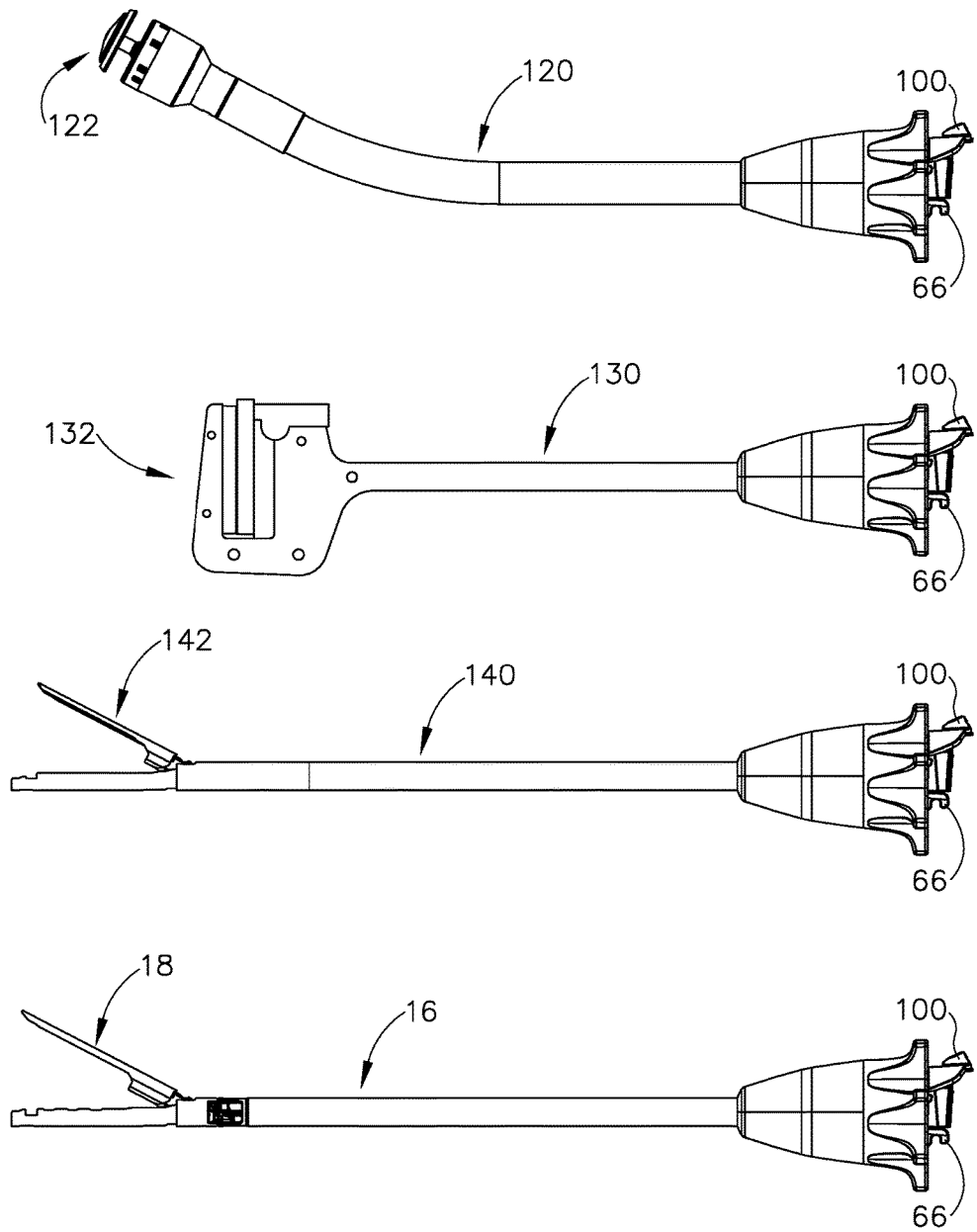
FIG. 6 depicts a side elevational view of an array of alternative shaft assemblies that may be used with the instrument of FIG. 1.

Handle assembly (11) may be configured for use in connection with interchangeable shaft assemblies that include end effectors that are adapted to support different sizes and types of staple cartridges, have different shaft lengths, sizes, and types, etc. By way of example only, FIG. 6 shows various different kinds of shaft assemblies (16, 120, 130, 140) that may be used with handle assembly (11). In particular, FIG. 6 shows a circular stapler shaft assembly (120) with an end effector (122) that is operable to perform a circular stapling operation (e.g., end-to-end anastomosis); a liner stapler shaft assembly (130) with an end effector (132) that is operable to perform a linear stapling operation; and a second endocutter shaft assembly (140) with an end effector (142) that is operable to perform the same kind of stapling and cutting operation as end effector (18). However, in this example, shaft assembly (140) is shorter than shaft assembly (16), shaft assembly (140) has a smaller diameter than shaft assembly (16), and end effector (142) is smaller than end effector (18). It should be understood that these various surgical stapling shaft assemblies (16, 120, 130, 140) are merely illustrative examples.

It should also be understood that control circuit (117) may be configured to detect the kind of shaft assembly (16, 120, 130, 140) coupled with handle assembly (11), and select a control algorithm suited for that particular kind of shaft assembly (16, 120, 130, 140). As another merely illustrative example, each shaft assembly (16, 120, 130, 140) may have a chip or other memory device storing the control algorithm suited for that particular kind of shaft assembly (16, 120, 130, 140); and control circuit (117) may receive and execute that control algorithm after shaft assembly (16, 120, 130, 140) is coupled with handle assembly (11).

In addition, handle assembly (11) may also be effectively employed with a variety of other interchangeable shaft assemblies including those assemblies that are configured to apply other motions and kinds of energy such as, for example, radio frequency (RF) energy, ultrasonic energy and/or motion to end effector arrangements adapted for use in connection with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

The various shaft assemblies (16) disclosed herein may employ sensors and various other components that require electrical communication with control circuit (117) in handled assembly (11). The electrical communications may be provided via mating electrical connectors (106, 108). By way of example only, such sensors and other components may be constructed and operable in accordance with at least some of the teachings of U.S. Pub. No. 2015/0272575, now U.S. Pat. No. 9,913,642, issued Mar. 13, 2018, the disclosure of which is incorporated by reference herein. In addition or in the alternative, instrument (10) may be constructed and operable in accordance with at least some of the teachings of any of the various other references that are cited herein.

It will be appreciated that the various teachings herein may also be effectively employed in connection with robotically-controlled surgical systems. Thus, the term "housing" or "body" may also encompass a housing, body, or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. By way of example only, the interchangeable shaft assemblies disclosed herein may be employed with any of the various robotic systems, instruments, components and methods disclosed in U.S. Pat. No. 9,072,535, entitled "Surgical Stapling Instruments with Rotatable Staple Deployment Arrangements," issued Jul. 7, 2015, the disclosure of which is incorporated by reference herein.

II. Exemplary Battery Life Display with Independent Power Source

As noted above, handle assembly (11) of the present example includes graphical user interface (116) that may be used to display information about the operational state of battery pack (110), the operational state of end effector (18), the operational state of articulation joint (52), the operational state of triggers (32, 33), and/or any other kinds of information. In some instances, it may be desirable to provide a secondary display that simply shows how much life remains in battery pack (110). Such a secondary display may be integrated into graphical user interface (116) or in battery pack (110). It may also be desirable for a secondary display to be powered independently of the rest of graphical user interface (116), motor (118), and control circuit (117); with a control circuit that is independent of the control circuit (117) that drives the rest of graphical user interface (116) and motor, etc. FIGS. 7-14, 16A, and 16B show some exemplary variations of handle assembly (11) that include a secondary display, referred to hereinafter as battery life display (216) for providing information regarding the remaining useful life or operational state of the primary drive battery of battery pack (110).

A. Exemplary Positioning of Battery Life Display

Figure 7:
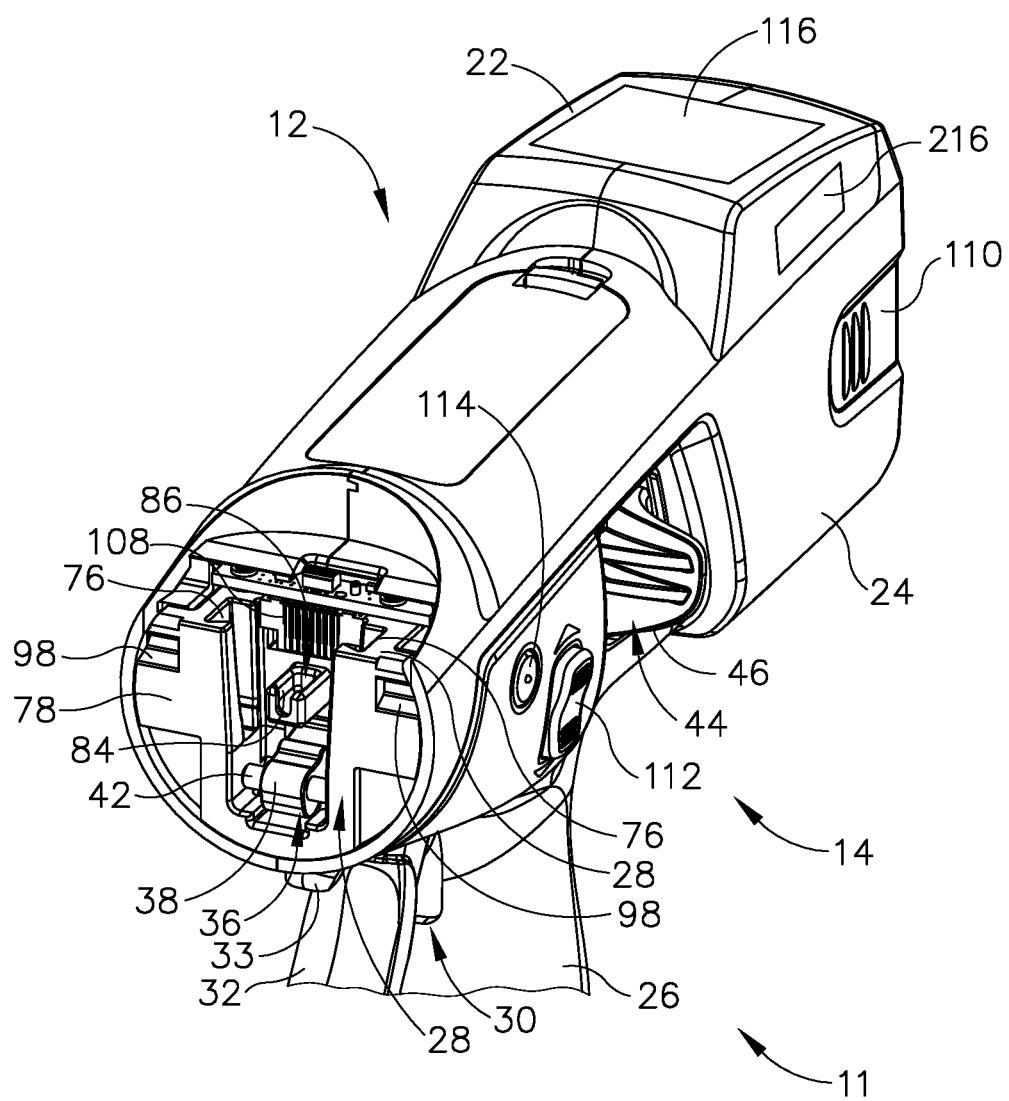
FIG. 7 depicts a partial perspective view of a variation of the handle assembly of the instrument of FIG. 1, with an exemplary battery life display disposed in a housing of the handle assembly.
Figure 8:
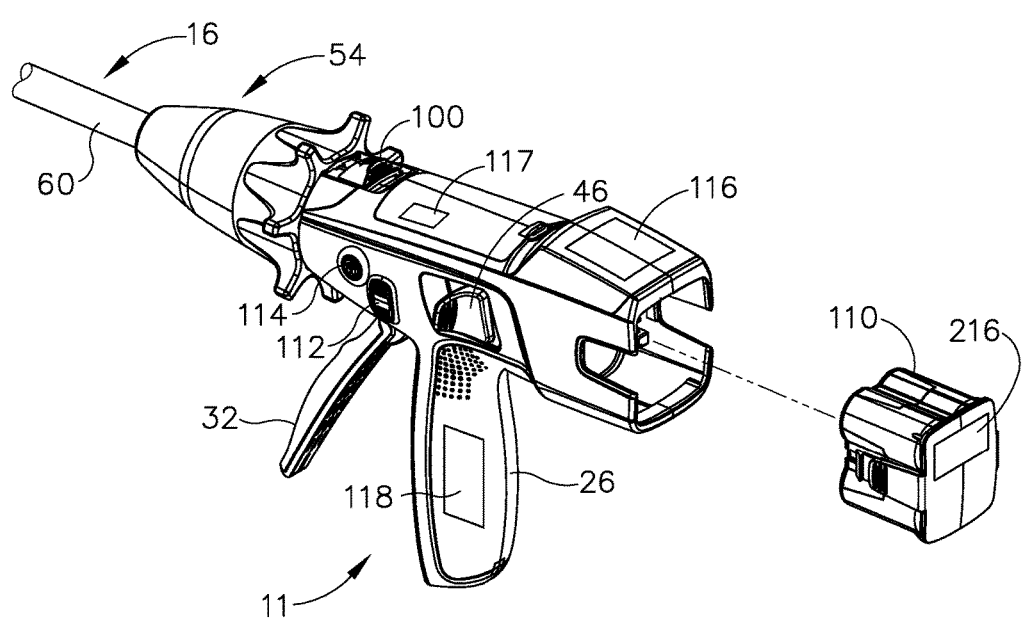
FIG. 8 depicts a perspective view of the proximal portion of the instrument of FIG. 1, with an exemplary alternative battery removed from the handle assembly and a battery life display disposed on the battery.
Figure 9:
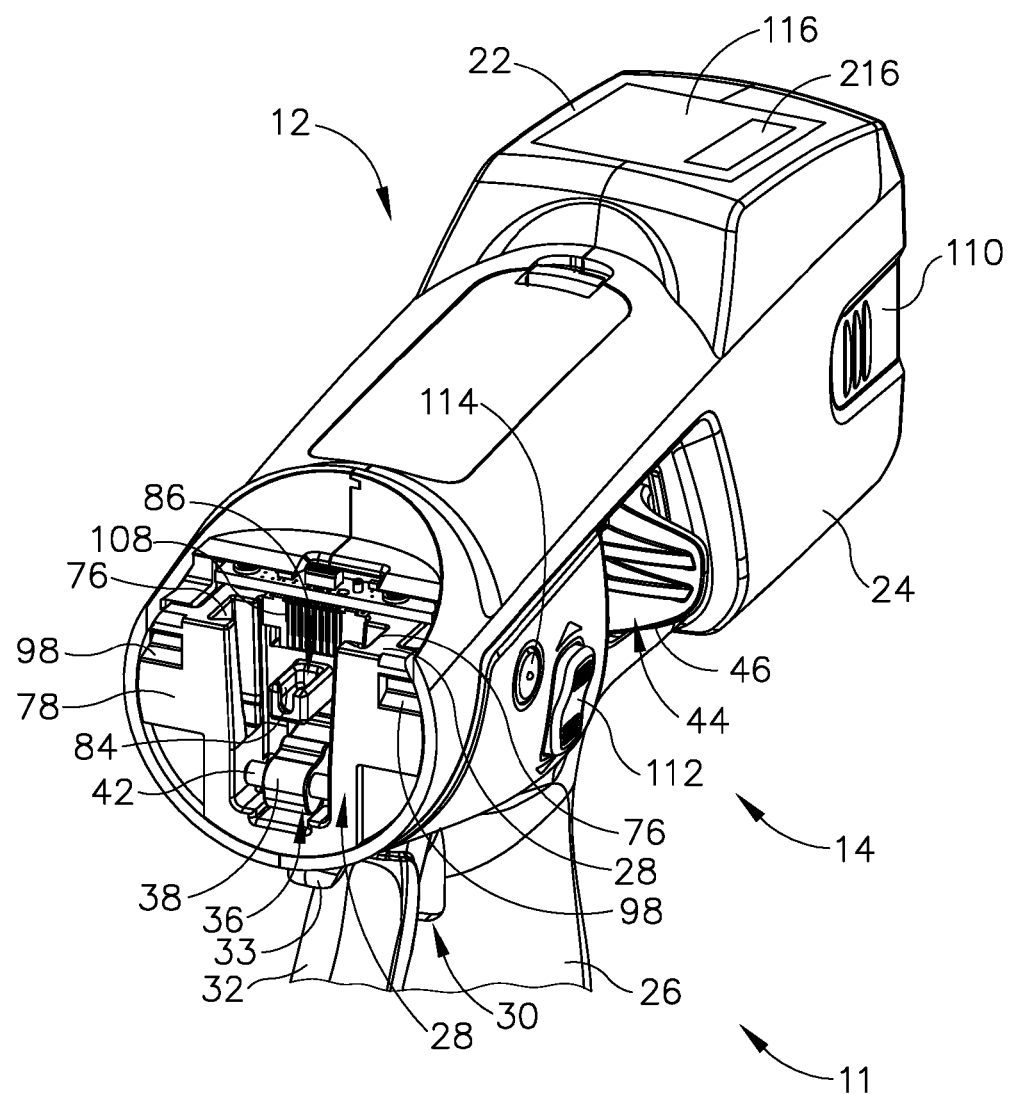
FIG. 9 depicts a partial perspective view of another variation of the handle assembly of the instrument of FIG. 1, with an exemplary battery life display integrated with an exemplary alternative graphical user interface.
Figure 10:
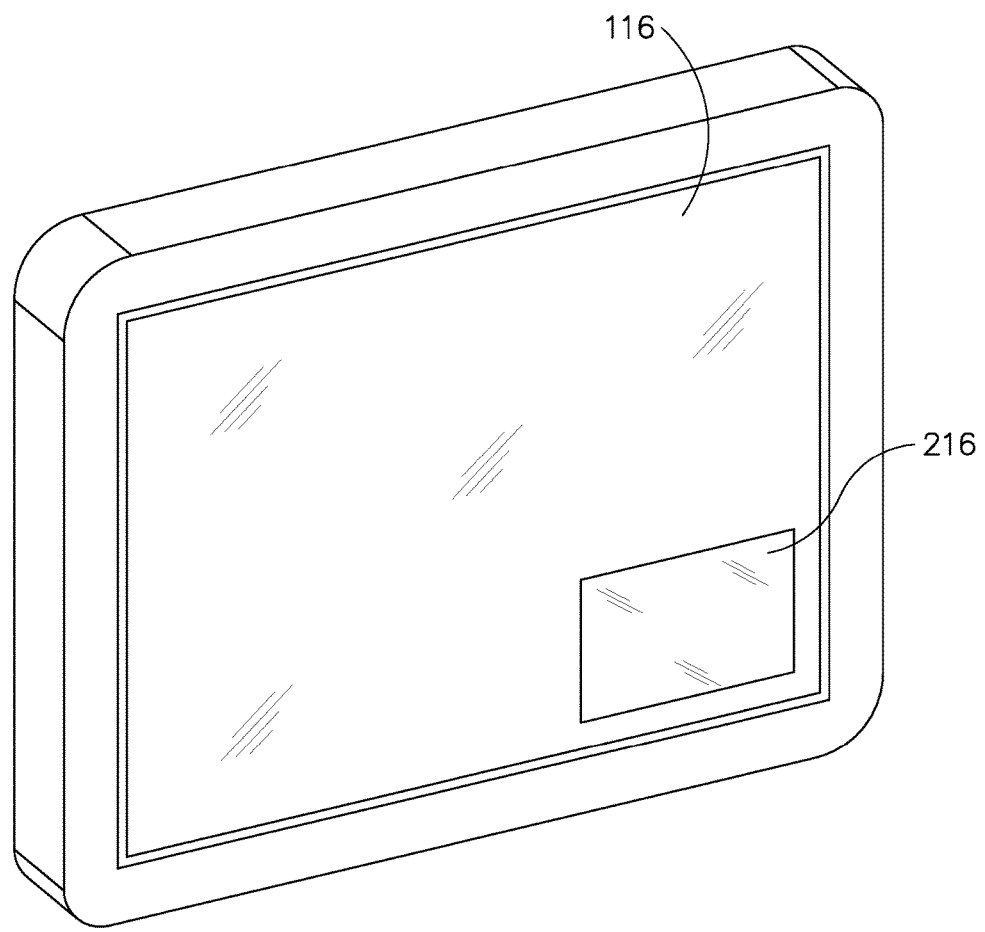
FIG. 10 depicts an enlarged elevational view of the battery life display and graphical user interface of FIG. 9.

As shown in FIGS. 7-10, some versions of handle assembly (11) may include battery life display (216) statically disposed or otherwise fixedly associated with handle assembly (11). This static version of battery life display (216) is configured to be integrated with handle assembly (11) or otherwise generally separately immovable from handle assembly (11). In some versions of handle assembly (11), battery life display (216) may be provided on either of interconnectable handle housing segments (22, 24), as shown in FIG. 7; or provided on battery pack (110), as shown in FIG. 8. As depicted in FIGS. 9 and 10, battery life display (216) may be provided as an integrated but segmented portion of graphical user interface (116).

In those versions where battery life display (216) is integrated with graphical user interface (116), battery life display (216) may be provided in any area of graphical user interface (116) and the relative position may be customizable as desired. For example, a user may manipulate a user input to configure battery life display (216) to be positioned in the lower right quadrant of graphical user interface (116), as shown in FIG. 10. Alternatively, another user may manipulate the user input to configure battery life display (216) to be positioned in the upper left quadrant of graphical user interface (116).

B. Exemplary Separate Power Source for Battery Life Display

As shown schematically in FIG. 11, while graphical user interface (116) is powered by a first or primary power source via battery pack (110), battery life display (216) is powered by a separate and secondary power source, referred to herein after as power source (210). In some versions, power source (210) is a dedicated power source distinct from the primary power source in battery pack (110). In this configuration, power source (210) may comprise a battery such as a coin cell battery or another style of battery sized to fit in handle assembly (11) or battery pack (110) (e.g., adjacent to primary cells in battery pack (110) that are used to drive operation of instrument (10)). In other versions, power source (210) is an intermediary power supply between battery life display (216) and the primary source of power provided in battery pack (110). In this configuration, power source (210) may be a small power reservoir (e.g., capacitor, supercapacitor, etc.) that can be recharged from the primary power source in battery pack (110) in response to the power level draining below a particular threshold. By way of example only, battery life display (216) may be independently powered in accordance with at least some of the teachings of U.S. patent application Ser. No. 15/480,546, entitled "Lifecycle Monitoring Features for Surgical Instrument," filed Apr. 6, 2017, now U.S. Patent Pub. No. 2017/0312044, published Nov. 2, 2017, the disclosure of which is incorporated by reference herein. As yet another merely illustrative variation, the same battery that drives main display (116) may drive life display (216), such that a separate dedicated life display power source (210) is not required. Even in instances where same power source is used to drive both kinds of displays (116, 216), the differences in configurations of associated circuits (117, 218) may result in life display (216) drawing less power from the power source than the amount of power drawn by main display (116).

Figure 11:
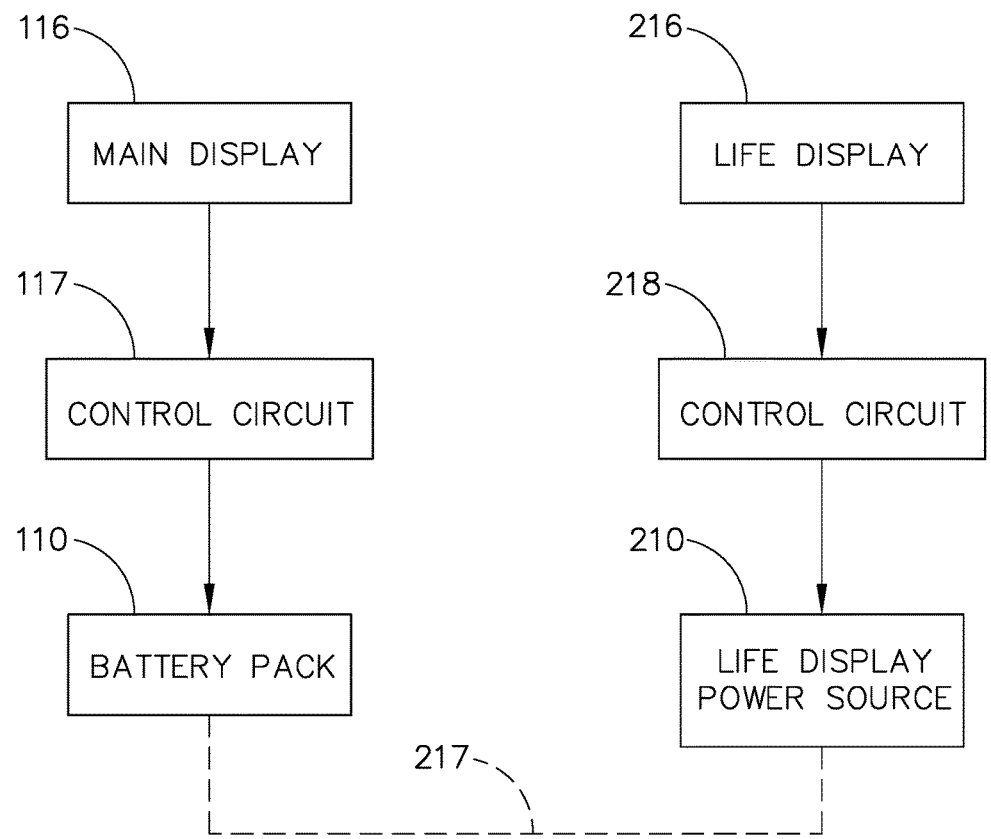
FIG. 11 depicts a schematic view of an exemplary battery life display, graphical user interface, exemplary power sources, and exemplary control circuit that may be used with the instrument of FIG. 1.

As shown in FIG. 11, a charge circuit (217) is provided to allow power source (210) access to the primary power source provided in battery pack (110), which provides power to graphical user interface (116). Some versions of power source (210) may be embodied as a rechargeable battery that is configured to supply power to battery life display (216) as needed. In these versions, power source (210) draws power from the primary power source in battery pack (110) through charge circuit (217) as needed to recharge power source (210).

C. Exemplary Tracking of Battery Life

As discussed above, handle assembly (11) may be a reusable component of instrument (10). However, while handle assembly (11) is reusable to a degree, handle assembly (11) may experience mechanical and/or electrical degradation over time. For example, the primary power source in battery pack (110) may eventually drain below a particular threshold value and may no longer be able to sufficiently power motor (118) to fire the end effector (18) connected to handle assembly (11). The gradual degradation may be correlated to a device life for handle assembly (11) and/or the primary power source in battery pack (110). The device life may be a static consideration (e.g. five firings of handle assembly (11)) or a dynamic consideration, depending on the particular usage of handle assembly (11).

A control circuit (218) may be contained within handle assembly (11) or battery pack (110). By way of example only, control circuit (218) may comprise a microcontroller and/or various other components as will be apparent to those of ordinary skill in the art in view of the teachings herein. Control circuit (218) is configured to store and execute algorithms for collecting metrics and characteristics of the various elements of instrument (10) and for thereafter calculating the amount of life remaining for either handle assembly (11) or the primary power source in battery pack (110). Control circuit (218) is also configured to drive battery life display (216) to display the calculated remaining life to the user. In some versions, control circuit (218) is configured to receive and process one or more signals from shaft assembly (16) and/or handle assembly (11) or any other elements within instrument (10). Other suitable ways in which control circuit (218) may be configured and operable will be apparent to those of ordinary skill in the art in view of the teachings herein. In some versions of handle assembly (11), control circuit (218) is omitted and any features or functionality described herein is provided through control circuit (117). In the present example, control circuit (218) is configured to draw less power to drive life display (216) than the power required by control circuit (117) to drive main display (116).

Battery life display (216) is configured to indicate the estimated remaining life of handle assembly (11) and/or the primary power source of battery pack (110) to the user. In order to provide the remaining life feedback to the user, control circuit (218) is configured to track various metrics or other usage characteristics of handle assembly (11) and calculate or update a device life variable. The device life variable is thereafter converted to a graphical feedback and provided to the user through battery life display (216) to indicate to the user the relative remaining life of handle assembly (11) and/or the primary power source of battery pack (110).

Figure 12:
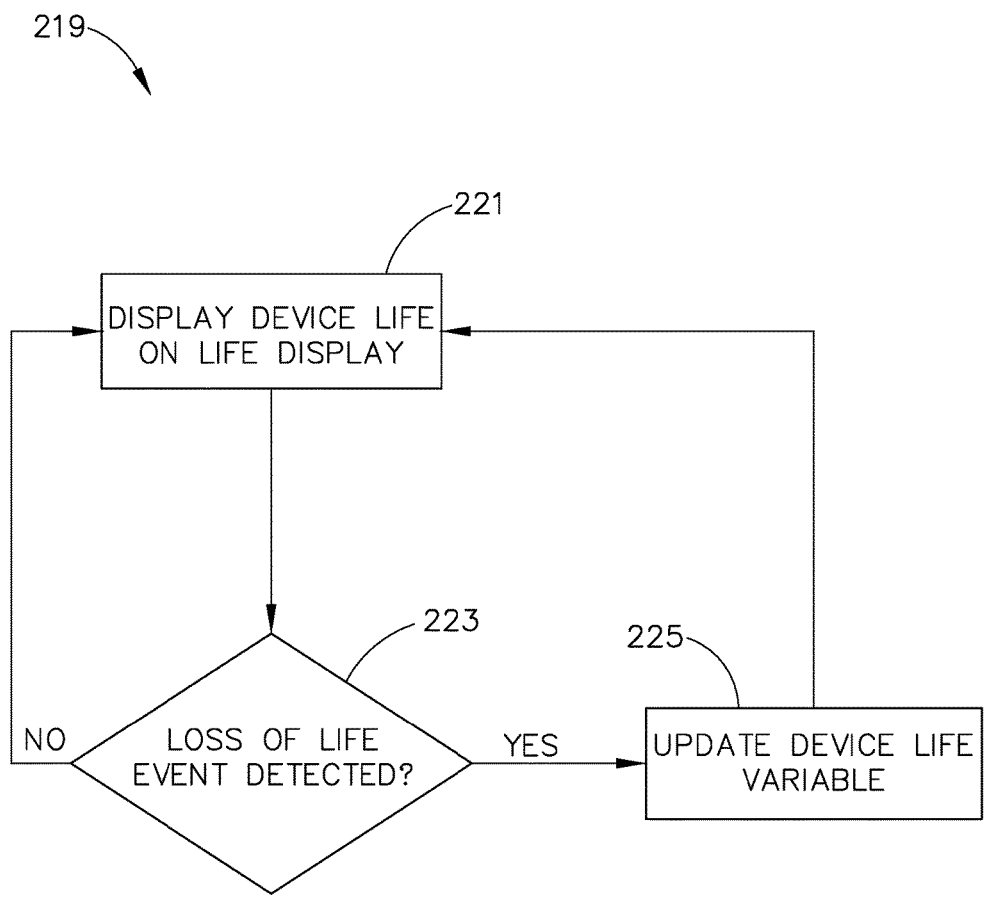
FIG. 12 depicts a flowchart of an exemplary method for providing device life information for the instrument of FIG. 1.

A general method (219) for continuously providing device life information is depicted in FIG. 12. Method (219) begins with a step (221), whereby the device life variable is displayed to the user on battery life display (216). Upon first use or first initialization of handle assembly (11), the device life variable indicates full life remaining for handle assembly (11).

In some versions of method (219), step (221) may be actuated or triggered by a request event, whereby the user either actively or passively requests to view the remaining life of handle assembly (11) and/or the primary power source in battery pack (110) via battery life display (216). In these versions of method (219), battery life display (216) is configured to sleep or dim to minimize power usage during the time between request events. Battery life display (216) will wake from the sleep or otherwise energize to provide feedback to the user upon the actuation of an active or passive request event. Examples of active request events may include depressing a button, activating graphical user interface (116), or actuating another element of instrument (10). Examples of passive request events may include a loss of life event such as those described below, an occurrence of a system event, reaching a threshold value with respect to an internal accelerometer, or when a particular internal counter reaches the next interval. Once the device life variable or a graphical representation thereof is displayed to the user, step (221) proceeds to a step (223).

In step (223) a decision is made regarding whether a loss of life event has been detected. In some versions of handle assembly (11), control circuit (117) will coordinate or provide this determination. In other versions, control circuit (218) will coordinate or provide this determination. In yet other versions, both control circuit (117) and control circuit (218) will coordinate or provide this determination. If a loss of life event is detected, step (223) proceeds to a step (225). If a loss of life event is not detected, step (223) proceeds back to step (221).

A loss of life event is an event recognizable to one or both of the control circuits (117, 218) as an event that will affect the remaining life of handle assembly (11) and/or the primary power source in battery pack (110). For example, a firing of handle assembly (11) may drain the primary power source in battery pack (110) and reduce the effective life of handle assembly (11) by an amount. Other examples of loss of life events include the mechanical toggling of a switch (not shown) of instrument (10); communication from graphical user interface (116) or handle assembly (11) when control circuit (117) indicates or recognizes a loss of life; or handle assembly (11) communicating either mechanically, electrically, or optically the next incremental loss of life as handle assembly (11) determines an amount of life has been used.

In some versions, battery life display (216) and/or control circuit (218) may access a low range current monitoring circuit associated with battery pack (110) while the primary power source in battery pack (110) is in a sleep mode, as discussed in greater detail below. In some versions, access to the low range current monitoring circuit is restricted to only while the primary power source in battery pack (110) is in the sleep mode. In these versions, battery life display (216) and/or control circuit (218) may access a primary circuit associated with the primary power source in battery pack (110) when the primary power source is not in the sleep mode. Battery life display (216) may be configured to display remaining lives associated with the primary power source on demand and may be powered by a dedicated coin cell power source or other kind of dedicated power source. By way of example only, the low range current monitoring circuit and/or the primary circuit disclosed herein may be employed with any of the various systems, instruments components and Change(s) plied methods disclosed in U.S. patent application Ser. No. 15/634,452, filed Jun. 27, 2017, entitled "Battery Powered Surgical Instrument with Dual Power Utilization Circuits for Dual Modes," filed on even date herewith, the disclosure of which is incorporated by reference herein.

After a loss of life event is detected, step (223) proceeds to step (225). In step (225), the device life variable is updated to reflect a change in the remaining life of handle assembly (11) and/or the primary power source in battery pack (110). Thereafter, step (225) proceeds back to step (221) to display the updated life information to the user via battery life display (216).

D. Exemplary Low Power Consumption Graphical Feedback

Figure 13A:
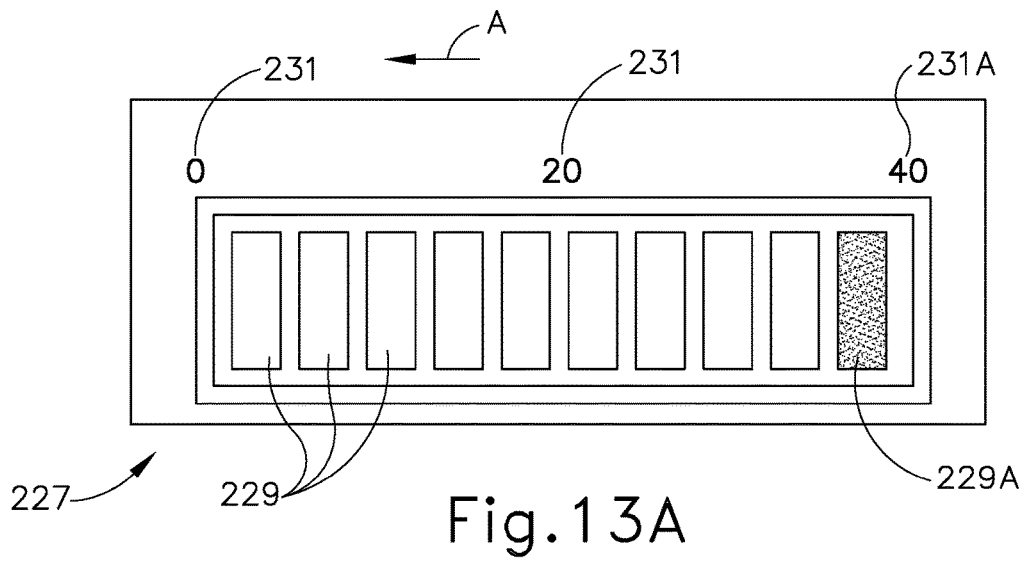
FIG. 13A depicts a diagrammatic view of an exemplary life meter style display for use in depicting device life information for the instrument of FIG. 1.

Battery life display (216) may be configured to minimize the power required to energize and depict the remaining life of handle assembly (11) and/or the primary power source in battery pack (110) in order to minimize the requirements of power source (210). To this end, battery life display (216) may include a graphically simple scheme to illustrate the remaining lives, such as a simple numeral or a pictorial representation of the relative remaining life of handle assembly (11) and/or the primary power source in battery pack (110). As shown in FIG. 13A, battery life display (216) may depict a life meter (227) to provide feedback information regarding the remaining life to the user. Life meter (227) includes a plurality of bars (229) extending from side to side with numerals (231) above to indicate the total number of lives remaining in handle assembly (11) and/or the primary power source in battery pack (110). One particular bar (229A) is illuminated in a different color from the remaining bars (229) to represent the total amount of lives left, when viewed in reference to numerals (231). In this example, bar (229A) is illuminated in a different color from the other bars (229) and is generally aligned with numeral (231A) to indicate there are "40" lives remaining. As lives are used in handle assembly (11) and/or the primary power source in battery pack (110), bar (229A) moves in the direction of Arrow A to indicate a decreasing amount of lives remain for handle assembly (11) and/or the primary power source in battery pack (110).

Figure 13B:
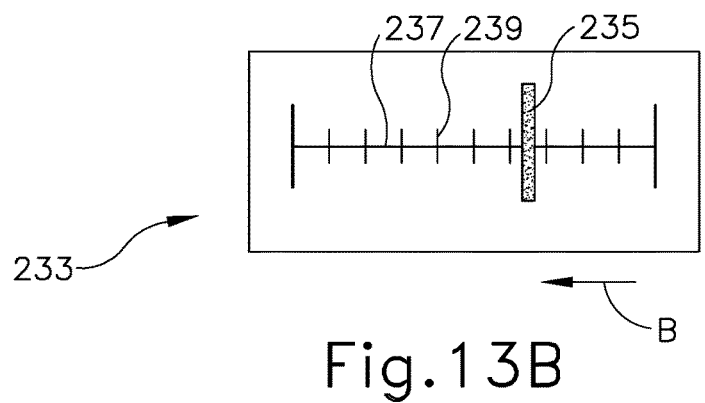
FIG. 13B depicts a diagrammatic view of an exemplary slider style display for use in depicting device life information for the instrument of FIG. 1.

As shown in FIG. 13B, battery life display (216) may depict a slider (233) to provide feedback information regarding the remaining life to the user. Slider (233) includes an indicator (235) juxtaposed with a track (237) having hash marks (239) to indicate lives remaining. As lives are spend/debited from handle assembly (11) and/or the primary power source in battery pack (110), indicator moves in the direction of Arrow B to illustrate the decrease in lives.

Figure 13C:
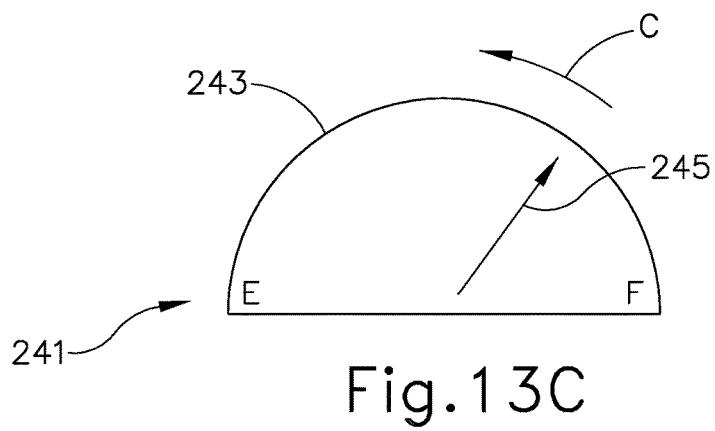
FIG. 13C depicts a diagrammatic view of an exemplary gauge style display for use in depicting device life information for the instrument of FIG. 1.

As shown in FIG. 13C, battery life display (216) may depict a gauge (241), reminiscent of an automobile style gas gauge or tachometer. Gauge (241) includes a dome shape (243) with an "E" graphic at one side of the dome to represent the battery lives are "Empty" and a "F" graphic at the other side to represent the battery lives are "Full." A needle (245) rotates to point in an area between the "F" and the "E" to illustrate how many lives remain in handle assembly (11) and/or the primary power source in battery pack (110) relative to the range of "Empty" to "Full." As lives are spent/debited from handle assembly (11) and/or the primary power source in battery pack (110), needle (245) rotates counter-clockwise in the direction of Arrow C to illustrate the decrease in lives.

As described above and shown in FIGS. 13A-13C, life meter (227), slider (233), and gauge (241) are merely examples of graphical feedback requiring a minimal amount of power from power source (210). Life meter (227), slider (233), and gauge (241) may be formed using electronic ink, LEDs, LCDs, or any other graphical technology. Further, any other style of graphically simple feedback may be provided by battery life display (216).

E. Exemplary Battery Modes

In some versions of handle assembly (11), the primary power source in battery pack (110) may transition between an active mode, a sleep mode, and a disposal mode. The primary power source in battery pack (110) transitions to the active mode when a user is handling handle assembly (11) or otherwise currently interacting with instrument (10). When handle assembly (11) senses a period of non-use, the primary power source in battery pack (110) will enter the sleep mode. In the sleep mode, handle assembly (11) will draw a minimum amount of power from the primary power source in battery pack (110) while waiting for a wake event such as the user picking up handle assembly (11) and actuating an internal accelerometer. When the useful life of handle assembly (11) and/or the primary power source in battery pack (110) decreases below a particular threshold, battery pack (110) moves to the disposal mode. In the disposal mode, battery pack (110) does not provide power to instrument (10). This ensures that instrument (10) does not fail or otherwise stop working in the middle of a medical procedure.

Figure 14:
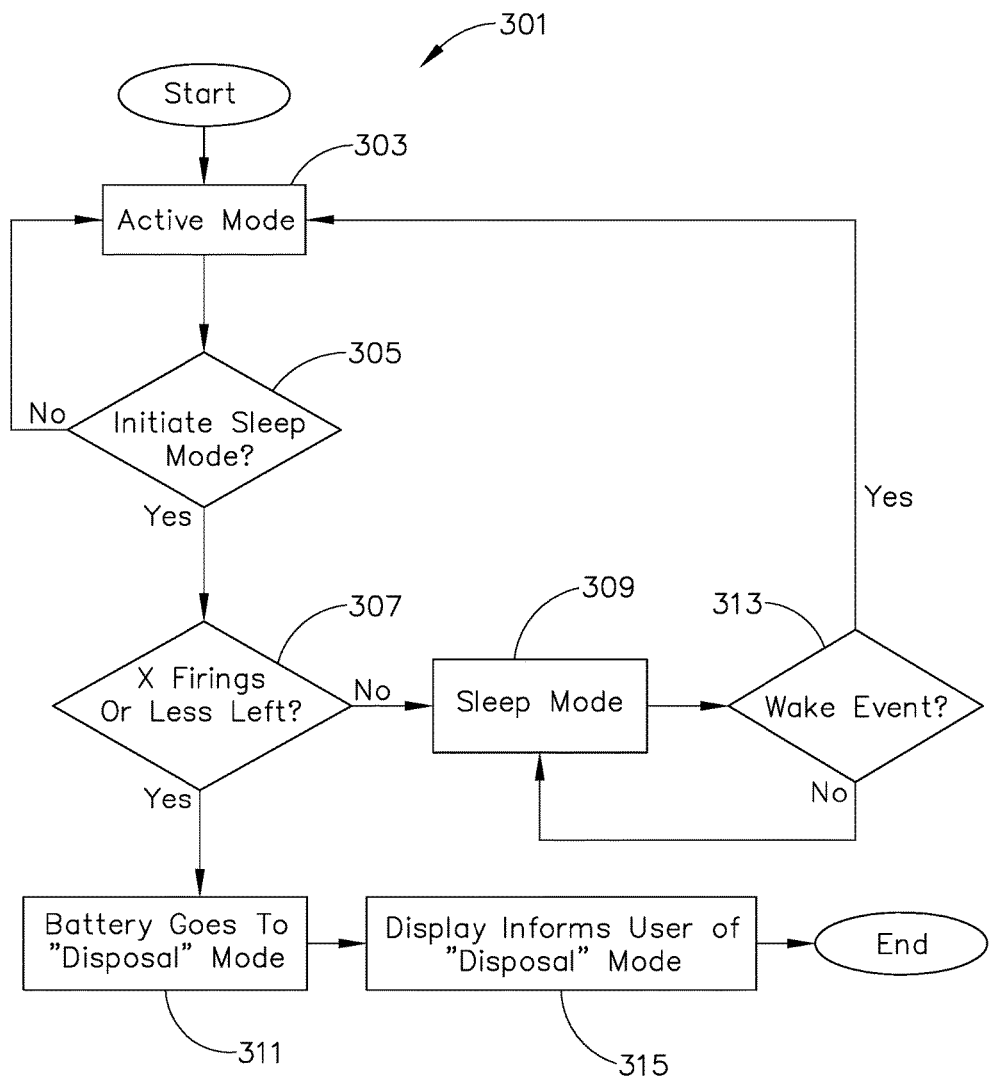
FIG. 14 depicts a flowchart of an exemplary method for transitioning between exemplary modes of the instrument of FIG. 1.

FIG. 14 illustrates a method (301) for used in some versions of handle assembly (11) and battery pack (110). Method (301) begins with a step (303), whereby handle assembly (11) is in the active mode. In the active mode, the user is either currently using, recently used, or preparing to use handle assembly (11) in some manner. After step (303), method (301) proceeds to a step (305). In step (305), a determination is made regarding whether the sleep mode should be initiated for handle assembly (11). This determination may be made on system metrics or other information available to control circuit (117) or control circuit (218). For example, handle assembly (11) may include an accelerometer and the determination may be made regarding whether to enter the sleep mode based on the amount of time that has elapsed since the accelerometer detected movement of handle assembly (11). If the determination is made that the sleep mode should not be initiated, step (305) proceeds back to step (303). If the determination is made that the sleep mode should be initiated, step (305) proceeds to a step (307).

In step (307), a determination is made regarding how many lives are left in handle assembly (11), the primary power source of battery pack (11), and/or how many more firings handle assembly (11) could undertake based on the remaining lives. The remaining firings and/or lives are thereafter compared to a particular threshold. For example, in some version of method (301), the threshold number of remaining firings is four. In this example, step (307) determines whether there are four firings or less remaining in handle assembly (11). If step (307) determines that there are more than four firings remaining in handle assembly (11), step (307) proceeds to a step (309) where the sleep mode is initiated for handle assembly (11). After the sleep mode is initiated, step (309) proceeds to a step (313). In step (313), a determination is made regarding whether handle assembly (11) has encountered a wake event, such as those described above. If it is determined that handle assembly (11) has not encountered a wake event, step (313) proceeds back to step (309). If it is determined that handle assembly (11) has encountered a wake event, step (313) proceeds back to step (303) and the active mode is initiated.

If step (307) determines that there are four firings or less remaining in handle assembly (11) and/or the primary power source in battery pack (110) based on the remaining lives, step (307) proceeds to a step (311). In step (311), battery pack (110) transitions into the disposal mode. In the disposal mode, battery operation of the primary power source in battery pack (110) is ceased and the elements of handle assembly (11) dependent on the primary power source in battery pack (110) will no longer function. Given the low remaining firings and life, the primary power source in battery pack (110) is treated as if it is fully depleted to ensure handle assembly (11) is no longer used and thus prevent handle assembly (11) from dying during a medical procedure. Thereafter, step (311) proceeds to a step (315). In step (315), feedback is provided to the user through graphical user interface (116) or battery life display (216) regarding the disposal mode of handle assembly (11)/battery pack (110). As noted above, battery life display (216) would be driven by power source (210) and control circuit (218) to indicate the transition to disposal mode.

III. Exemplary Movable Display

Positioning graphical user interface (116) on the top of handle assembly (11) may provide sufficient visibility for many users of instrument (10) in various surgical contexts. However, it may be desirable to enable a user to view graphical user interface (116) from various other angles. For instance, depending on the angle at which shaft assembly (16) is inserted in the patient, it may be desirable to facilitate viewing of graphical user interface (116) from the side or rear of handle assembly (11). Moreover, it may be desirable to enable the user to select the positioning and/or angle of graphical user interface (116), such that the user may make ad hoc adjustments based on the circumstances at hand. FIGS. 15A-21 show several illustrative variations of handle assembly (11) that include a movable display to allow the user to position the display as desired or for ergonomic purposes and/or for other purposes.

A. Exemplary Angular Movement of Display

Figure 15A:
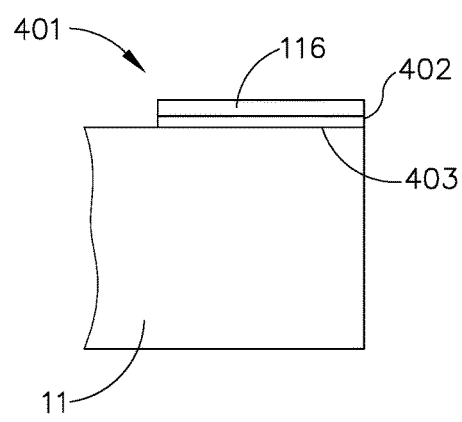
FIG. 15A depicts a side elevational view of the proximal portion of a variation of the instrument of FIG. 1, with an exemplary movable display in a first position.
Figure 15B:
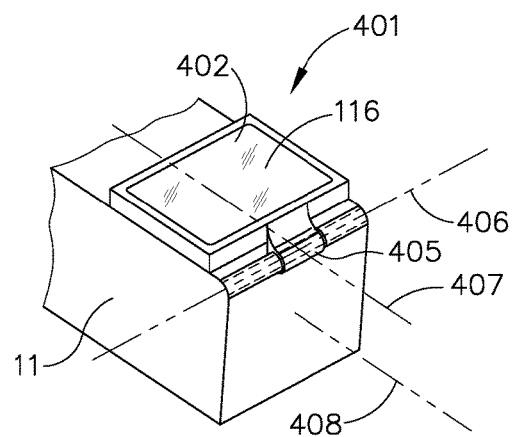
FIG. 15B depicts a perspective view of the proximal portion of the instrument of FIG. 15A, with the movable display in the first position.

As shown in FIGS. 15A-15G, handle assembly (11) may include a movable display (401). Movable display (401) is generally located at the proximal end of handle assembly (11) and includes a display portion (402) coupled with housing (12) of handle assembly (11) by way of a joint (405). Display portion (402) includes a display such as graphical user interface (116) within a housing (403). Joint (405) allows display portion (402) to move relative to handle assembly (11) about two axes of movement to position display potion (402) in any position desired by the user. Joint (405) allows display portion (402) to angularly move about a first axis (406), as shown in FIG. 15B. First axis (406) is generally orthogonal to a longitudinal axis of handle assembly (11), depicted in FIG. 15B as axis (408). Joint (405) also allows display portion (402) to angularly move about a second axis (407). Second axis (407) is generally co-planar with axis (408) and parallel with the longitudinal axis of handle assembly (11).

As shown in FIGS. 15A and 15B, display portion (402) is configured to selectively lay flat against the upper portion of housing (12). As desired, the user may manually lift display portion (402) into the orientation illustrated in FIG. 15C by moving display portion (402) about first axis (406) of joint (405) in the direction of Arrow D to project graphical user interface (116) proximally with respect to handle assembly (11). Thereafter, the user may move display portion (402) into the orientation illustrated in FIG. 15D by moving display portion (402) about second axis (407) of joint (405) in the direction of Arrow E. As shown in FIG. 15E, to project graphical user interface (116) distally with respect to handle assembly (11), the user continues to rotate display portion (402) in the direction of Arrow E. From the orientation illustrated in FIG. 15E, the user may move display portion (402) about joint (405) in the direction of Arrow F to fold display portion (402) against the proximal portion of handle assembly (11), as shown in FIGS. 15F and 15G. Thus, movable display (401) allows the user to determine the orientation of graphical user interface (116) and move graphical user interface (116) to their personal preference.

In some versions, detents or other features may be used to selectively retain movable display (401) at desired positions. Detents may be configured to provide enough resistance to prevent movable display (401) from inadvertently moving, yet still permit the user to adjust the positioning with relative ease. Further, an internal accelerometer or other sensor(s) may be provided to sense the position and/or orientation of movable display (401) and/or handle assembly (11) and change the orientation of the depicted information accordingly. For example, when the user moves movable display (401) sufficiently to turn movable display (401) upside down, the information in movable display (401) may rotate or adjust to provide the information in the correct orientation relative to the orientation of movable display (401).

Figure 15C:
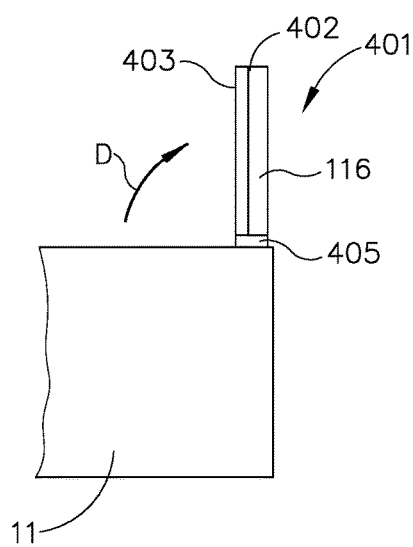
FIG. 15C depicts a side elevational view of the proximal portion of the instrument of FIG. 15A, with the movable display in a second position.
Figure 15D:
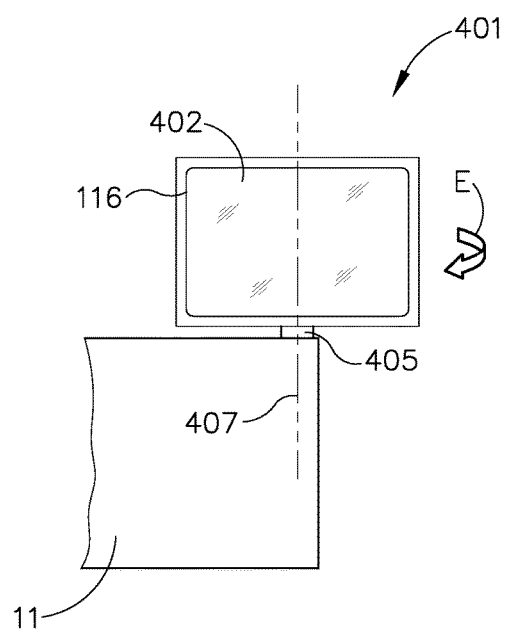
FIG. 15D depicts a side elevational view of the proximal portion of the instrument of FIG. 15A, with the movable display in a third position.
Figure 15E:
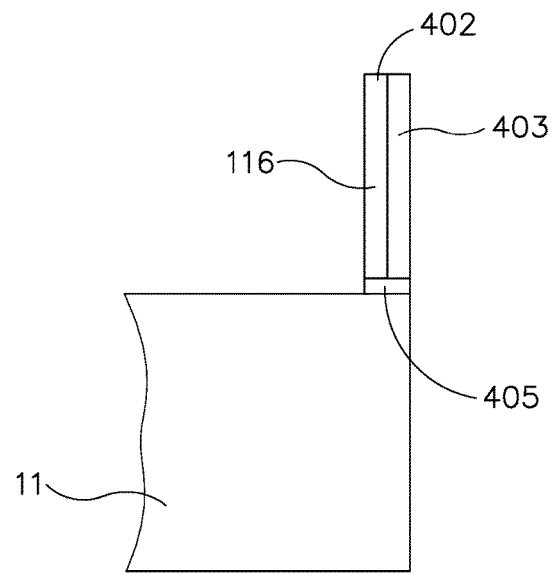
FIG. 15E depicts a side elevational view of the proximal portion of the instrument of FIG. 15A, with the movable display in a fourth position.
Figures 15F, 15G:
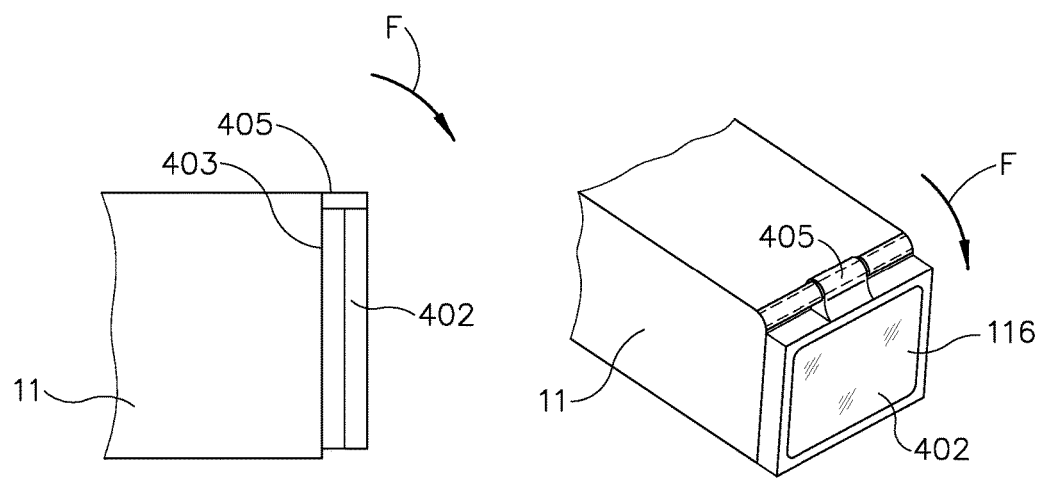
FIG. 15F depicts a side elevational view of the proximal portion of the instrument of FIG. 15A, with the movable display in a fifth position.
FIG. 15G depicts a perspective view of the proximal portion of the instrument of FIG. 15A, with the movable display in the fifth position.

In some versions of joint (405), movement of movable display (401) from FIG. 15C into the orientations shown in FIGS. 15A and 15B is prevented. Thus, movable display (401) may only transition between the orientation shown in FIG. 15E and the orientation shown in FIG. 15G. Some versions of joint (405) may be a single-axis joint, allowing pivotal movement only about first axis (406); while preventing movement of movable display (401) about second axis (407). In these versions of joint (405), movable display (401) pivots generally from FIG. 15E to FIG. 15F to FIG. 15G and back.

Figure 16A:
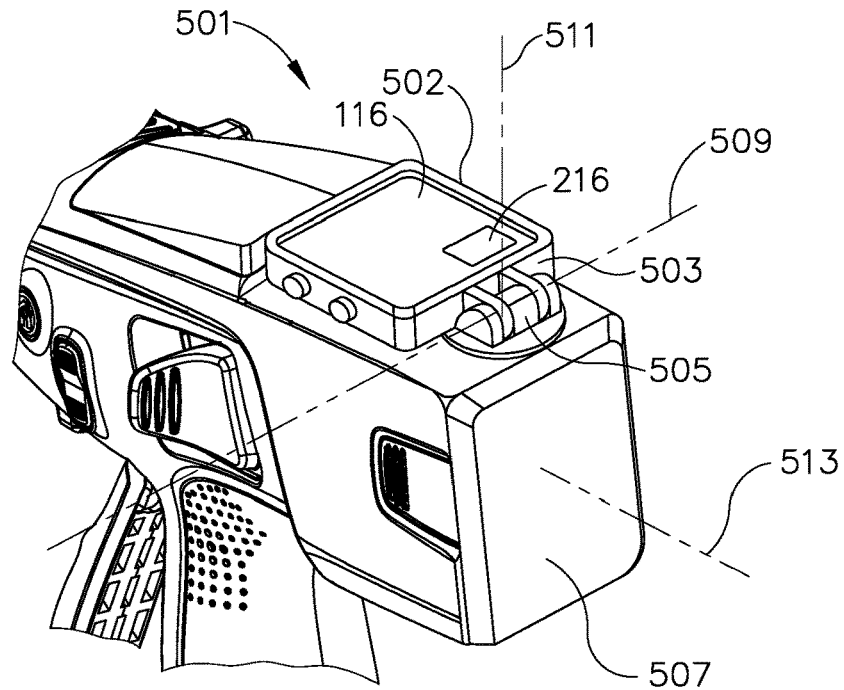
FIG. 16A depicts a perspective view of the proximal portion of another variation of the instrument of FIG. 1, with another exemplary movable display in a first position.
Figure 16B:
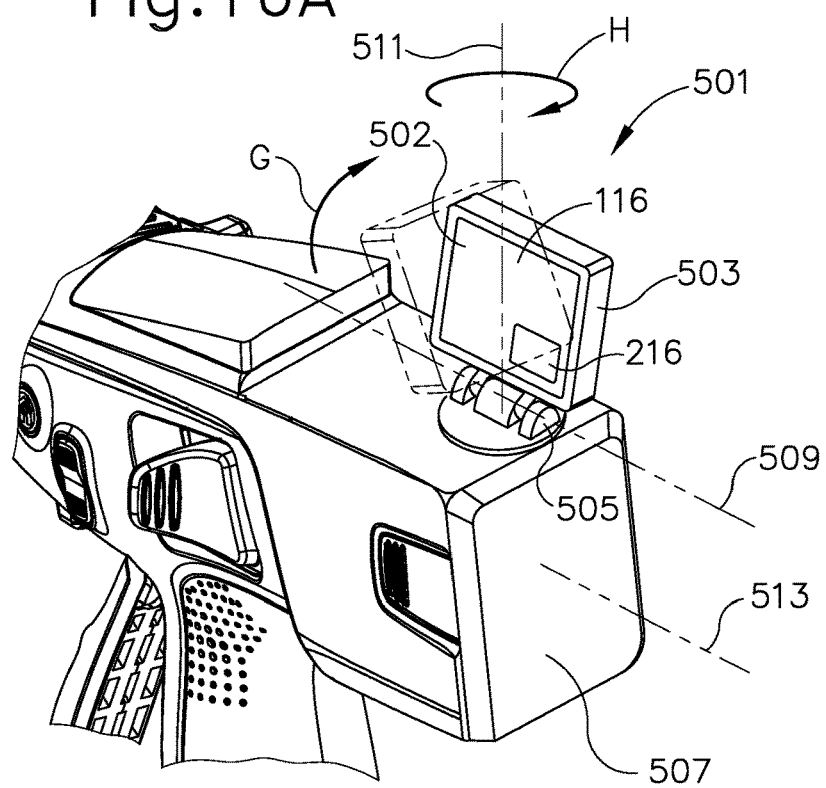
FIG. 16B depicts a perspective view of the instrument of FIG. 16A, with the movable display in a second position.

As shown in FIGS. 16A and 16B, handle assembly (11) may include a movable display (501). Similar to movable display (401), movable display (501) is generally located at the proximal end of handle assembly (11) and includes a display portion (502) within a housing (503) and coupled with housing (12) of handle assembly (11) by way of a joint (505). The orientation and range of motion of joint (505) differs from joint (405) in that joint (505) prevents display portion (502) from moving over the most proximal portion of handle assembly (11) and folding to abut the backside thereof. Within these confines, joint (505) allows for the movement of movable display (501) about a first axis (509) oriented generally orthogonally to a longitudinal axis (513) of handle assembly (11). Joint (505) also allows for the movement of movable display (501) about a second axis (511) oriented generally co-planar with longitudinal axis (513) and also orthogonal to the longitudinal axis of handle assembly (11).

As shown in FIG. 16B, display portion (502) is movable in the direction of Arrow G about first axis (509) and movable in the direction of Arrow H about second axis (511). However, due to the placement and configuration of joint (505), display portion (502) is prevented from moving beyond generally horizontal with the general plane of handle assembly (11). In some version of handle assembly (11), battery pack (110) is removably disposed in a battery compartment (507) and therefore it may be desired to prevent the user from covering battery compartment (507) with display portion (502). Thus, the user is prevented from moving display portion (502) into an overlapping relationship with battery compartment (507).

B. Exemplary Pivoting Display

As shown in FIGS. 17A-21, handle assembly (11) may include a display having a single axis angular movement, rather than a two-axis angular movement as illustrated with movable displays (401, 501).

Figure 17A:
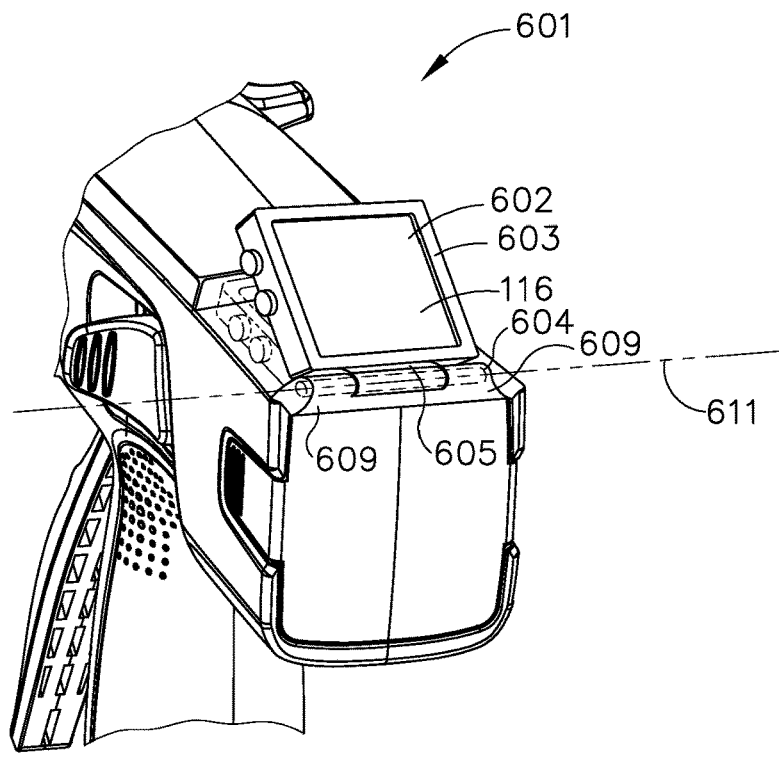
FIG. 17A depicts a perspective view of the proximal portion of another variation of the instrument of FIG. 1, with another exemplary movable display moving from a first position to a second position.
Figure 17B:
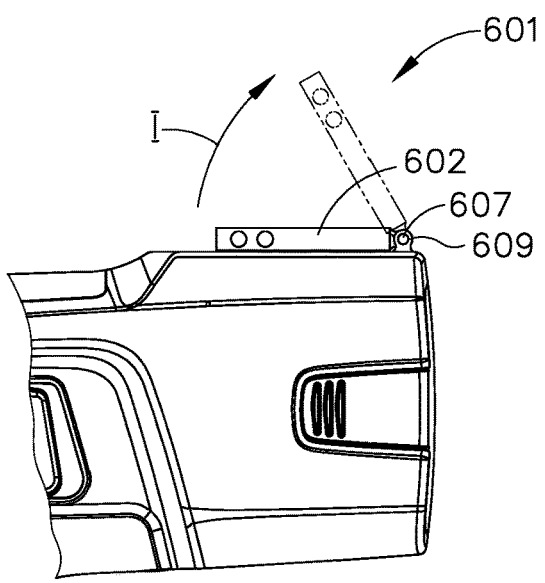
FIG. 17B depicts a side elevational view of the instrument of FIG. 17A, with the movable display moving from the first position to the second position.

A movable display (601) is shown in FIGS. 17A and 17B. Movable display (601) is generally located at the proximal end of handle assembly (11) and includes a display portion (602) coupled with housing (12) of handle assembly (11) by way of a pivot joint (605). Display portion (602) includes a display such as graphical user interface (116) within a housing (603). Pivot joint (605) allows display portion (602) to pivot relative to handle assembly (11) about an axis (611) and position display potion (602) in any position desired by the user along Arrow I of FIG. 17B. Pivot joint (605) includes a pin (607) disposed in a channel (not shown) defined by display portion (602) as well as a pair of recesses (not shown) defined by a pair of brackets (609) and generally aligned with the channel to allow display portion (602) to rotate about pin (607).

Figure 18:
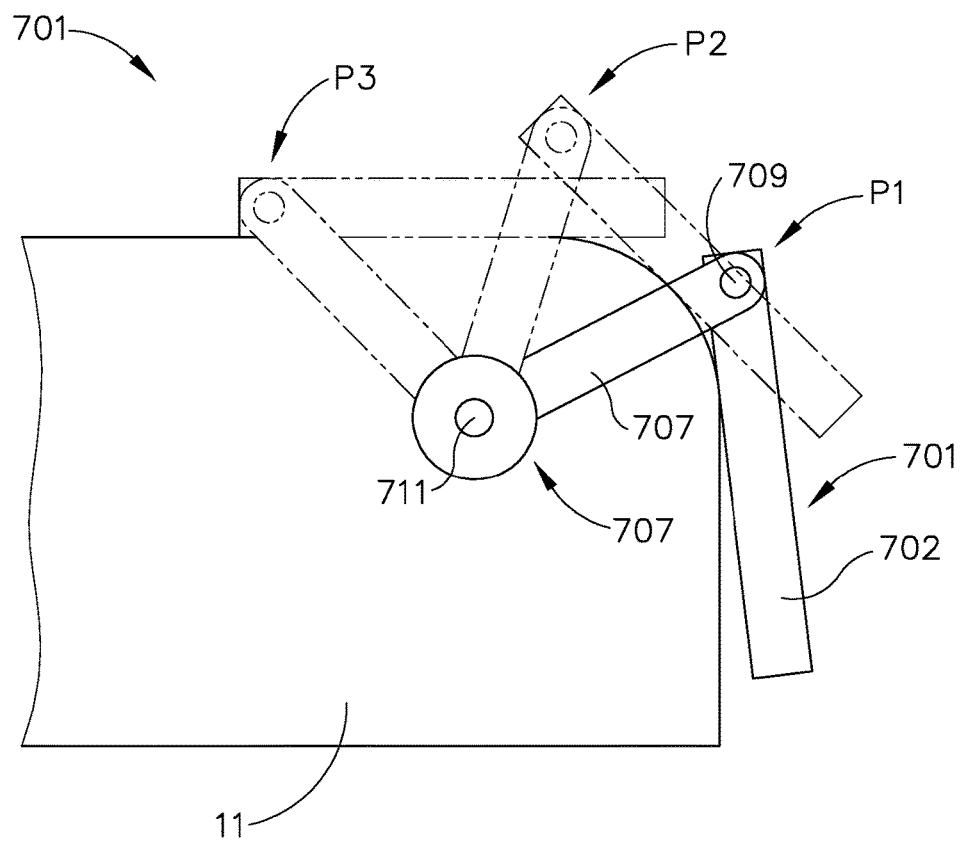
FIG. 18 depicts a side elevational view of the proximal portion of another variation of the instrument of FIG. 1, with another exemplary movable display moving between a first position, second position, and third position.
Figure 19A:
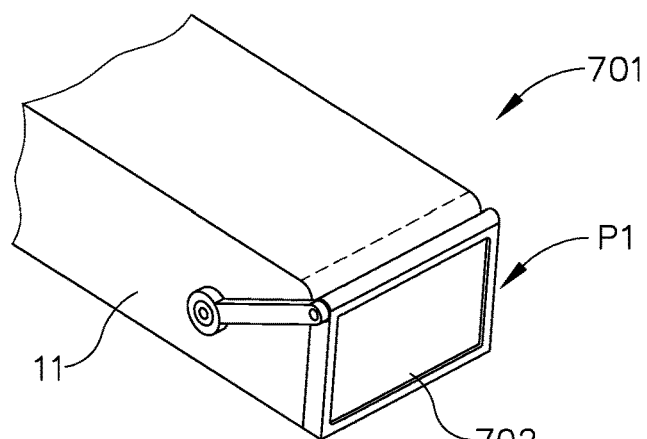
FIG. 19A depicts a perspective view of the proximal portion of the instrument of FIG. 18, with the movable display in the first position.
Figure 19B:
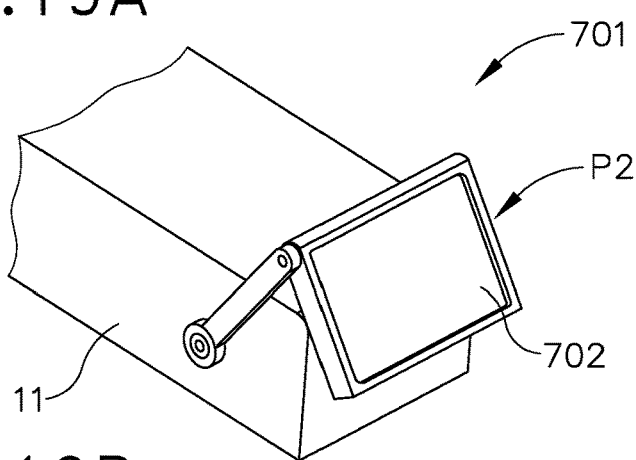
FIG. 19B depicts a perspective view of the proximal portion of the instrument of FIG. 18, with the movable display in the second position.
Figure 19C:
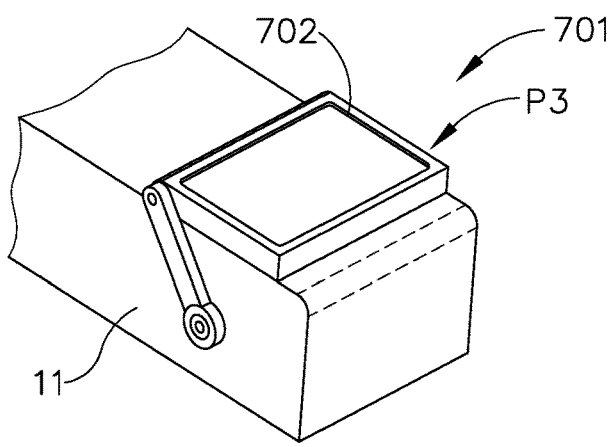
FIG. 19C depicts a perspective view of the proximal portion of the instrument of FIG. 18, with the movable display in the third position.

FIGS. 18-19C illustrate another movable display pivotable relative to handle assembly (11), referred to hereinafter as a movable display (701). Rather than pivot joint (605) having pin (607) disposed between two brackets (609), movable display (701) includes a guided slide mechanism (705). Guided slide mechanism (705) facilitates the slide pivoting of a display portion (702) between a first position (P1) (as shown in FIG. 19A), a second position (P2) (as shown in FIG. 19B), and a third position (P3) (as shown in FIG. 19C), and any intermediate position therebetween.

Guided slide mechanism includes a pair of display arms (707) connected to each side of display portion (702) by way of a first pivot connection (709). First pivot connection (709) may be any element that allows display arms (707) and display portion (702) to move as needed to move display portion (702) between first position (P1) and third position (P3). Each rotatable arm (707) is connected to handle assembly (11) by way of a second pivot connection (711). Second pivot connection (711) may be any element that allows display arms (707) and display portion (702) to move as needed to move display portion (702) between first position (P1) and third position (P3). As shown in FIGS. 19A-19C, guided slide mechanism (705) allows display portion (702) to move between the first position (P1), the second position (P2), and the third position (P3) to allow a user to position display portion (702) anywhere between the top of handle assembly (11), as shown in FIG. 19A, to the very most proximal end thereof, as shown in FIG. 19C.

Figure 20A:
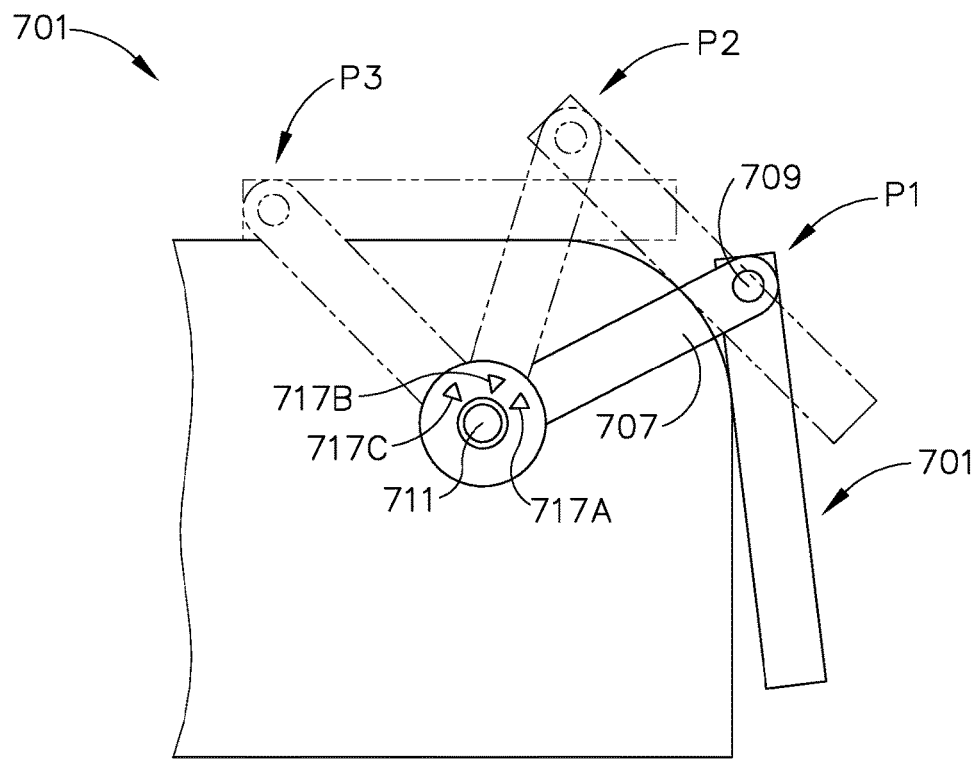
FIG. 20A depicts a side elevational view of the proximal portion of another variation of the instrument of FIG. 1, with another exemplary movable display moving between a first position, second position, and third position and with exemplary button locks aligned with the first position, second position, and third position.
Figure 20B:
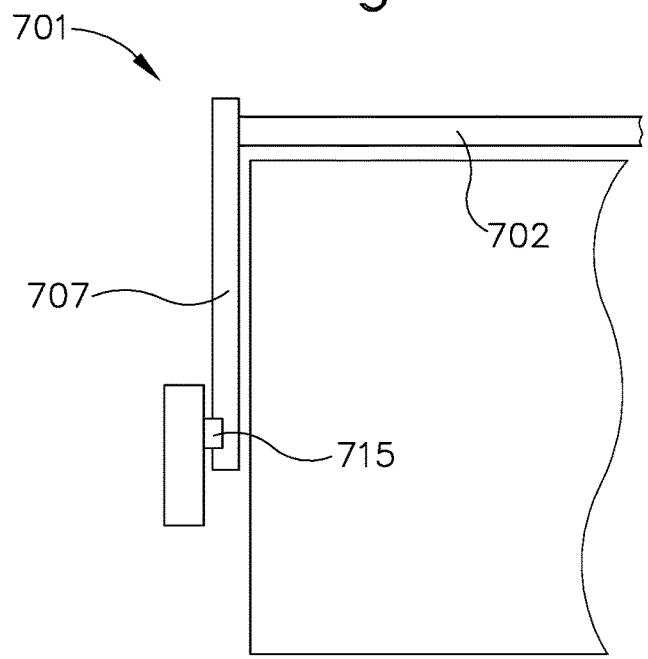
FIG. 20B depicts a rear elevational view of the instrument of FIG. 20A, with the movable display locked in the third position by one of the button locks.

Some versions of movable display (701) may include a locking mechanism (713) to allow a user to lock display arms (707) in a pre-selected orientation. As shown in FIGS. 20A and 20B, locking mechanism (713) may resemble a button lock, whereby a spring loaded button (715) is disposed on one or both display arms (707) facing handle assembly (11). A series of complementary button depressions (717) are aligned along the arcuate path of button (715) and configured to receive button (715) therein as a particular depression (717) aligns with button (715). Upon alignment, button (715) presses into depression (717) to lock guided mechanism (705) in the particular angular positon associated with the particular depression (717). For example, if a user wishes to lock display portion (702) in the first position (P1), the user will rotate display portion (702) until button (715) presses into depression (717A). If a user wishes to lock display portion (702) in the second position (P2), the user will rotate display portion (702) until button (715) presses into depression (717B). If a user wishes to lock display portion (702) in the third position (P3), the user will rotate display portion (702) until button (715) presses into depression (717C).

Figure 21:
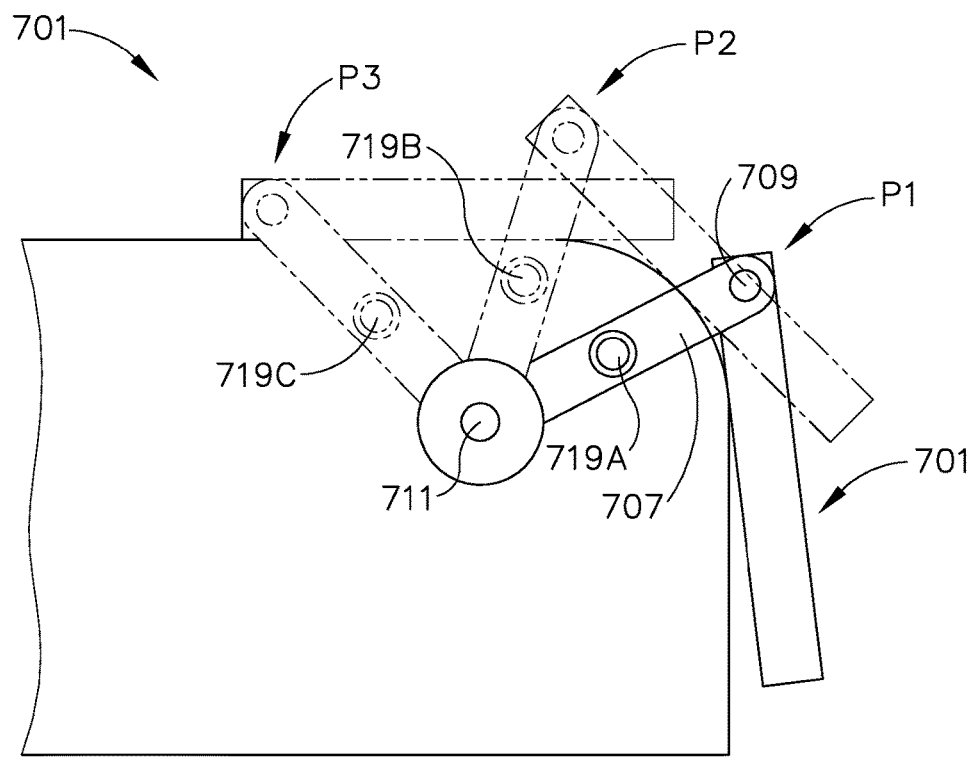
FIG. 21 depicts a side elevational view of the proximal portion of another variation of the instrument of FIG. 1, with another exemplary movable display moving between a first position, second position, and third position and with exemplary magnetic locks aligned with the first position, second position, and third position.

As shown in FIG. 21, locking mechanism (713) may resemble a magnetic lock, whereby a series of magnets (719) are disposed on handle assembly (11) along the arcuate path of display arms (707). In this configuration, display arms (707) are comprised of a ferromagnetic material and therefore attracted to magnets (719) as display arms (707) pass thereover.

For example, if a user wishes to lock display portion (702) in the first position (P1), the user will rotate display portion (702) until display arm (707) is magnetically attracted and held generally stationary by magnet (719A). If a user wishes to lock display portion (702) in the second position (P2), the user will rotate display portion (702) until display arm (707) is magnetically attracted and held generally stationary by magnet (719B). If a user wishes to lock display portion (702) in the third position (P3), the user will rotate display portion (702) until display arm (707) is magnetically attracted and held generally stationary by magnet (719C).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a handle assembly extending from a distal end to a proximal end; (b) a graphical user interface disposed on the handle assembly; (c) a primary circuit, wherein the primary circuit is operable to drive the graphical user interface; (d) a first power source, wherein the first power source is configured to provide power the graphical user interface; (e) a life display disposed on the handle assembly and operable to display a power level of the primary power source; and (f) a secondary circuit, wherein the secondary circuit is operable to drive the life display, wherein the secondary circuit is separate from the primary circuit, wherein the secondary circuit is configured to draw less power to drive the life display than an amount of power required by the first power source to drive the graphical user interface.

Example 2

The surgical instrument of Example 1, wherein the handle assembly includes a housing, wherein the graphical user interface is disposed in the housing.

Example 3

The surgical instrument of Example 2, wherein the life display is disposed in the housing.

Example 4

The surgical instrument of any one or more of Examples 1 through 2, further comprising a power source housing, wherein the handle assembly is configured to selectively receive the power source housing therein, wherein the first power source is disposed in the power source housing, wherein the life display is integrated into the power source housing.

Example 5

The surgical instrument of Example 4, further comprising a second power source, wherein the second power source is configured to provide power the life display, wherein the second power source is disposed in the power source housing.

Example 6

The surgical instrument of any one or more of Examples 1 through 5, wherein the life display is integrated with the graphical user interface.

Example 7

The surgical instrument of any one or more of Examples 1 through 6, wherein the graphical user interface is configured to graphically depict the life display at a position within the graphical user interface.

Example 8

The surgical instrument of Example 7, wherein the position is configurable by a user through the graphical user interface.

Example 9

The surgical instrument of any one or more of Examples 1 through 8, further comprising a control circuit, wherein the control circuit is configured to maintain a first power source life variable, wherein the life display is configured to graphically depict the first power source life variable.

Example 10

The surgical instrument of Example 9, wherein the handle assembly is configured to transition from an active mode to a disposal mode upon the first power source life variable reaching a threshold value.

Example 11

The surgical instrument of any one or more of Examples 1 through 10, further comprising a second power source, wherein the second power source is configured to provide power the life display, wherein the second power source is a rechargeable battery, wherein the second power source is configured to be recharged by the first power source.

Example 12

The surgical instrument of any one or more of Examples 1 through 11, further comprising a movable display, wherein one or both of the graphical user interface and the life display is disposed on the movable display.

Example 13

The surgical instrument of Example 12, wherein the movable display includes a joint, wherein the movable display is configured to angularly move about a first axis of the joint.

Example 14

The surgical instrument of Example 13, wherein the movable display is configured to angularly move about a second axis of the joint.

Example 15

The surgical instrument of any one or more of Examples 1 through 14, further comprising a second power source, wherein the second power source is configured to provide power the life display, wherein one or both of the first power source and the second power source is a battery.

Example 16

A surgical instrument comprising: (a) a handle assembly extending from a distal end to a proximal end; (b) a first display disposed on the handle assembly; (c) a first battery, wherein the first battery is configured to provide power the first display; (d) a second display disposed on the handle assembly, wherein the second display is configured to depict a battery life variable, wherein the battery life variable is based on a power level of the first battery; and (e) a second display power source, wherein the second display power source is configured to provide power the second display.

Example 17

The surgical instrument of Example 16, further comprising a control circuit coupled with the second display and second display power source.

Example 18

The surgical instrument of Example 17, wherein the battery life variable is maintained by the control circuit.

Example 19

A method of using a handle assembly having a first display and a second display, the method comprising: (a) powering the first display with a first power source; (b) powering the second display with a second power source; (c) assigning a number of lives to the first power source; and (d) depicting the number of lives on the second display.

Example 20

The method of Example 19, further comprising: (a) firing the handle assembly, wherein the firing is powered by the first power source; (b) in response to firing the handle assembly, decrementing the number of lives; and (c) in response to decrementing the number of lives, updating the number of lives depicted on the second display.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/634,385, filed Jun. 27, 2017, entitled "Apparatus and Method to Determine End of Life of Battery Powered Surgical Instrument," filed on even date herewith, the disclosure of which is incorporated by reference herein. Various suitable ways in which the teachings herein may be combined with the teachings of U.S. patent application Ser. No. 15/634,385, filed Jun. 27, 2017, will be apparent to those of ordinary skill in the art in view of the teachings herein.

In addition to the foregoing, the teachings herein may be readily combined with the teachings of U.S. patent application Ser. No. 15/634,436, filed Jun. 27, 2017, entitled "Battery Pack with Integrated Circuit Providing Sleep Mode to Battery Pack and Associated Surgical Instrument," filed on even date herewith, the disclosure of which is incorporated by reference herein. Various suitable ways in which the teachings herein may be combined with the teachings of U.S. patent application Ser. No. 15/634,436, filed Jun. 27, 2017, will be apparent to those of ordinary skill in the art in view of the teachings herein.

In addition to the foregoing, the teachings herein may be readily combined with the teachings of U.S. patent application Ser. No. 15/634,452, filed Jun. 27, 2017, entitled "Battery Powered Surgical Instrument with Dual Power Utilization Circuits for Dual Modes," filed on even date herewith, the disclosure of which is incorporated by reference herein. Various suitable ways in which the teachings herein may be combined with the teachings of U.S. patent application Ser. No. 15/634,452, filed Jun. 27, 2017, will be apparent to those of ordinary skill in the art in view of the teachings herein.

In addition to the foregoing, the teachings herein may be readily combined with the teachings of U.S. patent application Ser. No. 15/634,475, filed Jun. 27, 2017, entitled "Powered Surgical Instrument with Latching Feature Preventing Removal of Battery Pack," filed on even date herewith, the disclosure of which is incorporated by reference herein. Various suitable ways in which the teachings herein may be combined with the teachings of U.S. patent application Ser. No. 15/634,475, filed Jun. 27, 2017, will be apparent to those of ordinary skill in the art in view of the teachings herein.

In addition to the foregoing, the teachings herein may be readily combined with the teachings of U.S. patent application Ser. No. 15/634,497, filed Jun. 27, 2017, entitled "Modular Powered Electrical Connection for Surgical Instrument with Features to Prevent Electrical Discharge" filed on even date herewith, the disclosure of which is incorporated by reference herein. Various suitable ways in which the teachings herein may be combined with the teachings of U.S. patent application Ser. No. 15/634,497, filed Jun. 27, 2017, will be apparent to those of ordinary skill in the art in view of the teachings herein.

In addition to the foregoing, the teachings herein may be readily combined with the teachings of U.S. patent application Ser. No. 15/634,524, filed Jun. 27, 2017, entitled "Powered Surgical Instrument with Independent Selectively Applied Rotary and Linear Drivetrains," filed on even date herewith, the disclosure of which is incorporated by reference herein. Various suitable ways in which the teachings herein may be combined with the teachings of U.S. patent application Ser. No. 15/634,524, filed Jun. 27, 2017, will be apparent to those of ordinary skill in the art in view of the teachings herein.

In addition to the foregoing, the teachings herein may be readily combined with the teachings of U.S. patent application Ser. No. 15/634,556, filed Jun. 27, 2017, entitled "Powered Circular Stapler with Reciprocating Drive Member to Provide Independent Stapling and Cutting of Tissue," filed on even date herewith, the disclosure of which is incorporated by reference herein. Various suitable ways in which the teachings herein may be combined with the teachings of U.S. patent application Ser. No. 15/634,556, filed Jun. 27, 2017, will be apparent to those of ordinary skill in the art in view of the teachings herein.

In addition to the foregoing, the teachings herein may be readily combined with the teachings of U.S. patent application Ser. No. 15/934,620, filed Jun. 27, 2017, entitled "Surgical Stapler with Independently Actuated Drivers to Provide Varying Staple Heights," filed on even date herewith, the disclosure of which is incorporated by reference herein. Various suitable ways in which the teachings herein may be combined with the teachings of U.S. patent application Ser. No. 15/934,620, filed Jun. 27, 2017, will be apparent to those of ordinary skill in the art in view of the teachings herein.

In addition to the foregoing, the teachings herein may be readily combined with the teachings of U.S. patent application Ser. No. 15/634,589, filed Jun. 27, 2017, entitled "Surgical Instrument Handle Assembly with Feature to Clean Electrical Contacts at Modular Shaft Interface," filed on even date herewith, the disclosure of which is incorporated by reference herein. Various suitable ways in which the teachings herein may be combined with the teachings of U.S. patent application Ser. No. 15/634,589, filed Jun. 27, 2017, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
    (a) a handle assembly extending from a distal end to a proximal end;
    (b) a graphical user interface disposed on the handle assembly;
    (c) a primary circuit, wherein the primary circuit is operable to drive the graphical user interface;
    (d) a first power source, wherein the primary circuit is configured to draw a first amount of power directly from the first power source to drive the graphical user interface;
    (e) a life display disposed on the handle assembly and operable to display a power level of the first power source;
    (f) a secondary circuit, wherein the secondary circuit is operable to drive the life display, wherein the secondary circuit is separate from the primary circuit; and
    (g) a second power source, wherein the secondary circuit is configured to draw a second amount of power directly from the second power source to drive the life display, wherein the second amount of power is less than the first amount of power.

2. The surgical instrument of claim 1, wherein the handle assembly includes a housing, wherein the graphical user interface is disposed in the housing.

3. The surgical instrument of claim 2, wherein the life display is disposed in the housing.

4. The surgical instrument of claim 2, further comprising a power source housing, wherein the handle assembly is configured to selectively receive the power source housing therein, wherein the first power source is disposed in the power source housing, wherein the life display is integrated into the power source housing.

5. The surgical instrument of claim 4, wherein the second power source is disposed in the power source housing.

6. The surgical instrument of claim 1, wherein the life display is integrated with the graphical user interface.

7. The surgical instrument of claim 1, wherein the graphical user interface is configured to graphically depict the life display at a position within the graphical user interface.

8. The surgical instrument of claim 7, wherein the position is configurable by a user through the graphical user interface.

9. The surgical instrument of claim 1, further comprising a control circuit, wherein the control circuit is configured to maintain a first power source life variable, wherein the life display is configured to graphically depict the first power source life variable.

10. The surgical instrument of claim 9, wherein the handle assembly is configured to transition from an active mode to a disposal mode upon the first power source life variable reaching a threshold value.

11. The surgical instrument of claim 1, wherein the second power source is a rechargeable battery, wherein the second power source is configured to be recharged by the first power source.

12. The surgical instrument of claim 1, further comprising a movable display, wherein one or both of the graphical user interface and the life display is disposed on the movable display.

13. The surgical instrument of claim 12, wherein the movable display includes a joint, wherein the movable display is configured to angularly move about a first axis of the joint.

14. The surgical instrument of claim 13, wherein the movable display is configured to angularly move about a second axis of the joint.

15. The surgical instrument of claim 1, wherein one or both of the first power source and the second power source is a battery.

16. A surgical instrument comprising:
    (a) a handle assembly extending from a distal end to a proximal end;
    (b) a first display disposed on the handle assembly;
    (c) a first battery, wherein the first battery is configured to provide power to the first display;
    (d) a second display disposed on the handle assembly, wherein the second display is configured to depict a battery life variable, wherein the battery life variable is based on a power level of the first battery; and
    (e) a second display power source, wherein the second display power source is configured to provide power to the second display and not the first display.

17. The surgical instrument of claim 16, further comprising a control circuit coupled with the second display and the second display power source.

18. The surgical instrument of claim 17, wherein the battery life variable is maintained by the control circuit.

19. A method of using a surgical instrument that includes a handle assembly having a first display and a second display, the method comprising:
    (a) powering the first display with a first power source;
    (b) powering the second display with a second power source; and
    (c) depicting on the second display an element that indicates a remaining life of the first power source and not the second power source.

20. The method of claim 19, further comprising:
    (a) firing the handle assembly, wherein the firing is powered by the first power source such that the firing decreases a remaining life of the first power source; and (b) in response to firing the handle assembly, altering the element depicted on the second display to reflect the decrease in remaining life of the first power source.

* * * * *